(12) United States Patent
Mohanakrishnan et al.

(10) Patent No.: US 9,508,004 B2
(45) Date of Patent: Nov. 29, 2016

(54) EYE GAZE DETECTION APPARATUS, COMPUTER-READABLE RECORDING MEDIUM STORING EYE GAZE DETECTION PROGRAM AND EYE GAZE DETECTION METHOD

(71) Applicant: FUJITSU LIMITED, Kawasaki-shi, Kanagawa (JP)

(72) Inventors: Jaikrishna Mohanakrishnan, Kawasaki (JP); Akinori Taguchi, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 0 days.

(21) Appl. No.: 14/672,903

(22) Filed: Mar. 30, 2015

(65) Prior Publication Data

US 2015/0294148 A1 Oct. 15, 2015

(30) Foreign Application Priority Data

Apr. 9, 2014 (JP) .................. 2014-080440

(51) Int. Cl.
*G06K 9/00* (2006.01)
(52) U.S. Cl.
CPC ......... *G06K 9/00604* (2013.01); *G06K 9/0061* (2013.01); *G06K 9/00261* (2013.01)
(58) Field of Classification Search
CPC combination set(s) only.
See application file for complete search history.

(56) References Cited

U.S. PATENT DOCUMENTS

| | | | |
|---|---|---|---|
| 6,094,498 A | 7/2000 | Okumura | |
| 2002/0191818 A1 | 12/2002 | Matsuo et al. | |
| 2007/0247524 A1* | 10/2007 | Yoshinaga | G06K 9/0061 348/78 |
| 2008/0232693 A1* | 9/2008 | Guan | G06K 9/00228 382/190 |
| 2011/0069277 A1 | 3/2011 | Blixt et al. | |
| 2012/0218398 A1 | 8/2012 | Mehra | |

FOREIGN PATENT DOCUMENTS

| | | |
|---|---|---|
| EP | 2 052 676 A1 | 4/2009 |
| JP | 2001-22933 | 1/2001 |
| JP | 2001-43382 | 2/2001 |
| JP | 2001-167284 | 6/2001 |
| JP | 2003-44853 | 2/2003 |
| JP | 2012-239550 | 12/2012 |
| JP | 2013-45151 | 3/2013 |

OTHER PUBLICATIONS

Extended European Search Report issued Aug. 19, 2015 in corresponding European Patent Application No. 15161526.7.

* cited by examiner

*Primary Examiner* — Alex Liew
(74) *Attorney, Agent, or Firm* — Staas & Halsey LLP

(57) ABSTRACT

An eye-gaze-detection apparatus includes an image acquisition unit that acquires a face image of a user from an imaging apparatus, the face image being captured by the imaging apparatus; a feature-quantity extraction unit that extracts a feature quantity of the face image; an eye-gaze-calculation-determination unit that determines whether or not an eye-gaze calculation process is performed by referring to a rule database, based on the feature quantity extracted by the feature quantity extraction unit, the rule database storing a rule set associating a condition including the feature quantity of the face image with information indicating whether or not the eye gaze calculation process is performed; and an eye-gaze-calculation unit that performs the eye-gaze-calculation process for the user, based on the feature quantity of the face image acquired by the image acquisition unit, when the eye-gaze-calculation-determination unit determines that the eye-gaze-calculation process is performed.

20 Claims, 30 Drawing Sheets

FIG. 6

| TIME (hh:mm:ss.ms) | CANDIDATE AREA |
|---|---|
| 00:00:01.033 | [(10, 10), (10, 12), (100, 14), (100, 12), (100, 15)] |
| 00:00:01.066 | [(10, 10), (11, 12), (100, 12), (98, 12), (99, 15)] |
| 00:00:01.099 | [(9, 9), (10, 12), (100, 14), (101, 12), (99, 15)] |

FIG. 7

| PATTERN NAMES | CONDITIONS | NEED OF GAZE CALCULATION |
|---|---|---|
| USER'S EYE REMAINS STATIONARY | THE NUMBER OF CANDIDATE AREAS AND POSITION IN EXTRACTED IMAGE IS THE SAME AS THOSE IN PREVIOUS IMAGE, AND DEGREE OF COINCIDENCE OF PERIPHERAL AREA OF CANDIDATE AREA IS EQUAL TO OR GREATER THAN 95% | NO NEED |
| USER'S EYE IS BLINKING | THE NUMBER OF CANDIDATE AREAS IN EXTRACTED IMAGE IS CHANGED EQUAL TO OR MORE THAN CERTAIN NUMBER OF CANDIDATE AREAS IN PREVIOUS IMAGE AND DISTANCE OF Y COORDINATE OF CHANGED CANDIDATE AREA IS WITHIN CERTAIN VALUE | NO NEED |
| OTHERS | OTHER THAN ABOVE CONDITIONS | NEED |

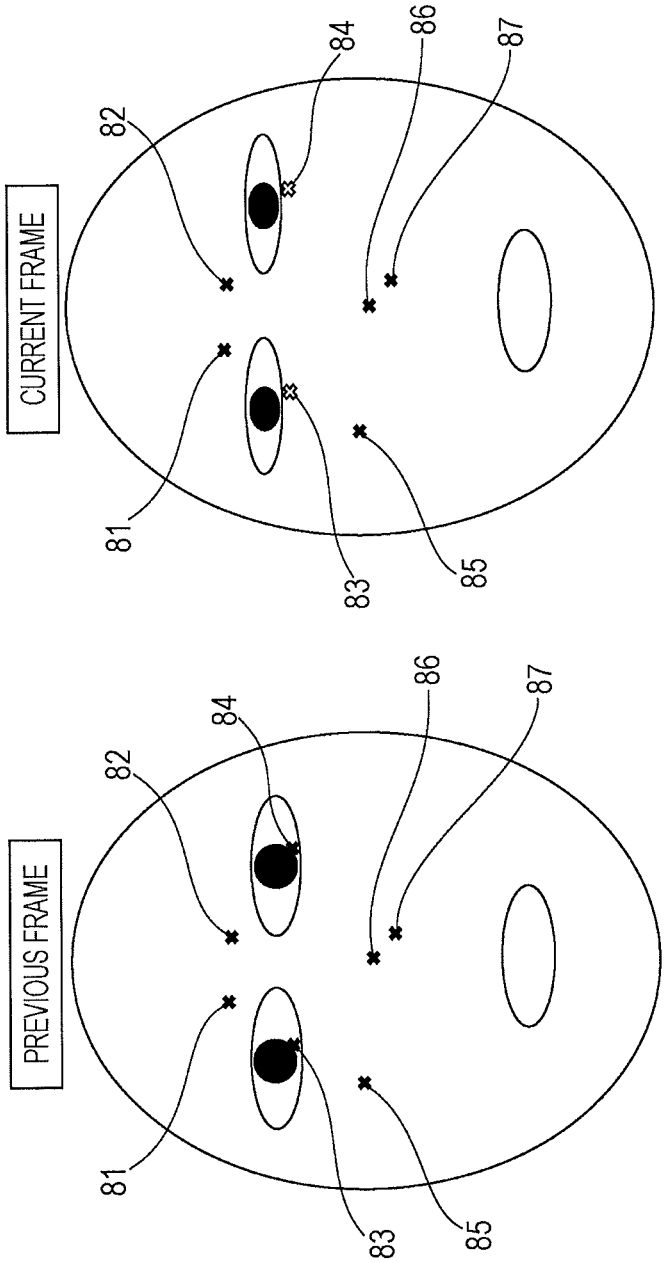

FIG. 11

| CAPTURING TIME | FRAME NAME |
|---|---|
| 00:00:00.033 | FRAME 1 |
| 00:00:00.099 | FRAME 3 |

| PATTERN NAMES | CONDITIONS | NEED OF GAZE CALCULATION |
|---|---|---|
| USER IS LOOKING SIDEWAYS | WHITE PIXEL WHICH IS EQUAL TO OR MORE THAN N IS PRESENT IN ONE SIDE OF CORNEAL REFLECTION CANDIDATE AREAS OF BOTH EYES | NO NEED |
| OTHERS | OTHER THAN ABOVE CONDITION | NEED |

| PATTERN NAMES | CONDITIONS | NEED OF GAZE CALCULATION |
|---|---|---|
| EYE GAZE MOVEMENT CALCULATION IS NOT POSSIBLE | FACE AREA IS SMALLER THAN THRESHOLD OR CORNEAL REFLECTION CANDIDATE AREA IS NOT PRESENT IN FACE AREA | NO NEED |
| OTHERS | OTHER THAN ABOVE CONDITION | NEED |

| CAPTURING TIME | FRAME | PRIORITY |
|---|---|---|
| 00:00:00.033 | FRAME 1 | 100 |
| 00:00:00.099 | FRAME 3 | 10 |
| 00:00:00.132 | FRAME 4 | 50 |

201

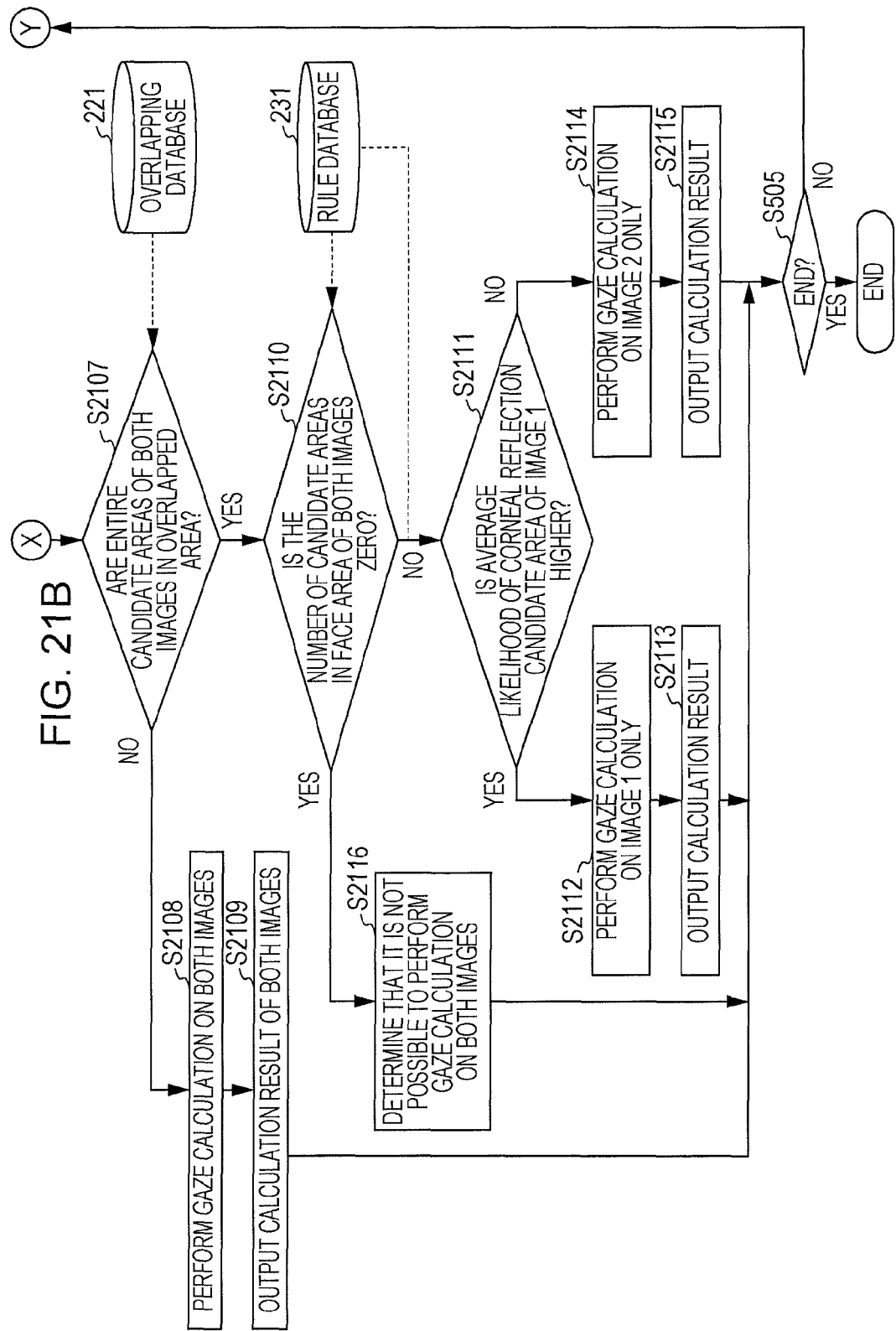

FIG. 22

| CAMERA NAMES | OVERLAPPED AREA |
|---|---|
| CAMERA 1<br>CAMERA 2 | CAMERA 1 – [(440, 0) TO (640, 480)]<br>CAMERA 2 – [(0, 0) TO (200, 480)] |
| CAMERA 2<br>CAMERA 3 | CAMERA 2 – [(440, 0) TO (640, 480)]<br>CAMERA 3 – [(0, 0) TO (200, 480)] |
| CAMERA 4<br>CAMERA 5 | CAMERA 4 – [(440, 0) TO (640, 480)]<br>CAMERA 5 – [(0, 0) TO (200, 480)] |

FIG. 23

| PATTERN NAMES | CONDITIONS | NEED OF GAZE CALCULATION |
|---|---|---|
| EYE GAZE MOVEMENT CALCULATION IS NOT POSSIBLE | NO CORNEAL REFLECTION CANDIDATE AREA IN BOTH IMAGES | NO NEED FOR BOTH IMAGES |
| DETERIORATION OF ACCURACY OF EYE GAZE | LESS CORNEAL REFLECTION CANDIDATE AREAS DUE TO OTHER OVERLAPPED CAMERAS | NO NEED FOR IMAGE HAVING LESS CANDIDATE AREAS |
| OTHERS | OTHER THAN ABOVE CONDITIONS | NEED |

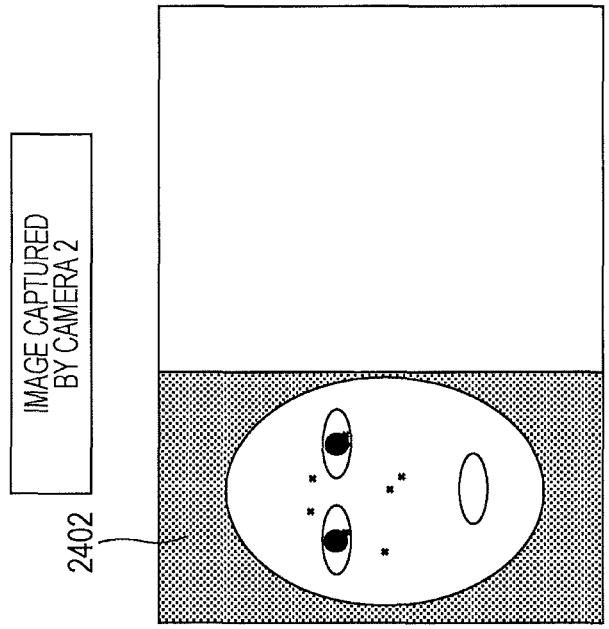
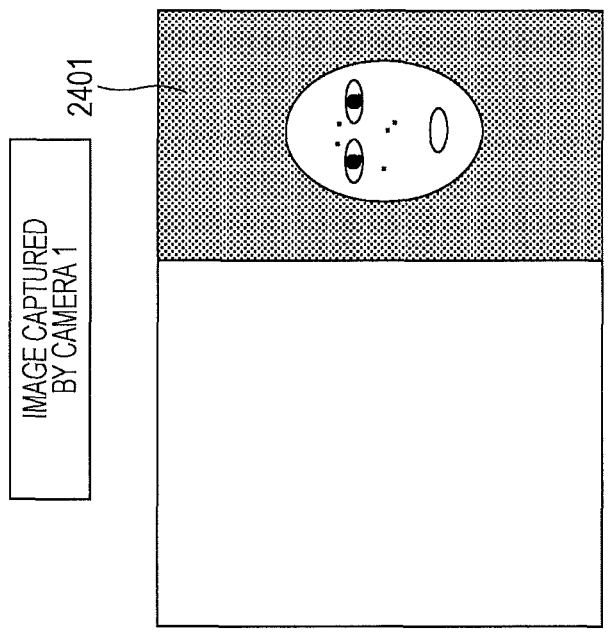

EYE GAZE DETECTION APPARATUS, COMPUTER-READABLE RECORDING MEDIUM STORING EYE GAZE DETECTION PROGRAM AND EYE GAZE DETECTION METHOD

CROSS-REFERENCE TO RELATED APPLICATION

This application is based upon and claims the benefit of priority of the prior Japanese Patent Application No. 2014-080440 filed on Apr. 9, 2014, the entire contents of which are incorporated herein by reference.

FIELD

The embodiments discussed herein are related to an eye gaze detection apparatus, a computer-readable recording medium storing an eye gaze detection program, and an eye gaze detection method for detecting a user's eye gaze.

BACKGROUND

In the related art, an eye gaze detection technology for detecting the user's eye gaze or the line of sight is used in an input interface, determination of a user's state, or the like. For example, the input interface is used as a technology for detecting the user's eye gaze as data and operating icons on a screen of a computer by using the detected eye gaze data. In addition, the determination of the user's state is used in a technology for detecting a user's eye gaze while driving a vehicle and then outputting an alarm by determining whether or not a driver looks aside while driving.

Particularly, the eye gaze detection technology using a non-contact type camera or the like reduces an operation load on a user and thus is widely used. For example, there is a corneal reflection method for detecting an eye gaze by extracting a corneal reflection area of the user from an image captured by a camera. As an application technology for the above technology, a technology for selecting an optimal corneal reflection area by removing an area acquired by the reflection of a spectacle lens in a plurality of candidates of corneal reflection areas is disclosed (for example, refer to Japanese Laid-open Patent Publication No. 2012-239550).

In addition, as a technology related to the eye gaze detection technology, the following technologies are disclosed. A technology for detecting and tracing an eye and an eye blink from an image of a user's face (for example, refer to Japanese Laid-open Patent Publication No. 2001-43382).

A technology for extracting a partial image which is considered to include a face image from a target image based on an edge image extracted from the target image, and determining whether or not the extracted partial image includes the face image by referring to a learning dictionary that holds learning information for identifying the face image and a non-face image (for example, refer to Japanese Laid-open Patent Publication No. 2003-44853).

A technology for detecting a user's eyeball from the target image by moving a template image in which the eyeball is modeled by using genetic algorithms to each portion on the target image which is the image of a user's face to perform template matching (for example, refer to Japanese Laid-open Patent Publication No. 2013-45151).

A technology for more accurately extracting a contour of an eye from an input face image of a user by using a two-dimensional template (for example, refer to Japanese Laid-open Patent Publication No. 2001-22933).

A technology for detecting a reflection illumination part of the glasses from a captured image of a user wearing glasses (for example, refer to Japanese Laid-open Patent Publication No. 2001-167284).

SUMMARY

According to an aspect of the invention, an eye gaze detection apparatus includes an image acquisition unit that acquires a face image of a user from an imaging apparatus, the face image being captured by the imaging apparatus; a feature quantity extraction unit that extracts a feature quantity of the face image acquired by the image acquisition unit; an eye gaze calculation determination unit that determines whether or not an eye gaze calculation process for the user is performed by referring to a rule database, based on the feature quantity extracted by the feature quantity extraction unit, the rule database storing a rule set associating a condition including the feature quantity of the face image with information indicating whether or not the eye gaze calculation process is performed; and an eye gaze calculation unit that performs the eye gaze calculation process for the user, based on the feature quantity of the face image acquired by the image acquisition unit, when the eye gaze calculation determination unit determines that the eye gaze calculation process is performed.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 6 is a diagram illustrating an example of a candidate area database;

FIG. 7 is a diagram illustrating an example of a rule database (part 1);

FIGS. 8A and 8B are diagrams illustrating an example of a face image when it is determined that a user is blinking his or her eye;

FIG. 11 is a diagram illustrating an example of a processing database (part 1);

FIG. 14 is a diagram illustrating an example of a rule database (part 2);

FIG. 18 is a diagram illustrating an example of the rule database (part 3);

FIG. 20 is a diagram illustrating an example of the processing database (part 2);

FIGS. 21A and 21B are flowcharts illustrating an eye gaze detection process by serial processing performed by a computer of an eye gaze detection apparatus according to the sixth embodiment;

FIG. 22 is a diagram illustrating an example of an overlapping database;

FIG. 23 is a diagram illustrating an example of the rule database (part 4);

FIGS. 24A and 24B are diagrams illustrating an example of an overlapped image;

DESCRIPTION OF EMBODIMENTS

Figure 1:
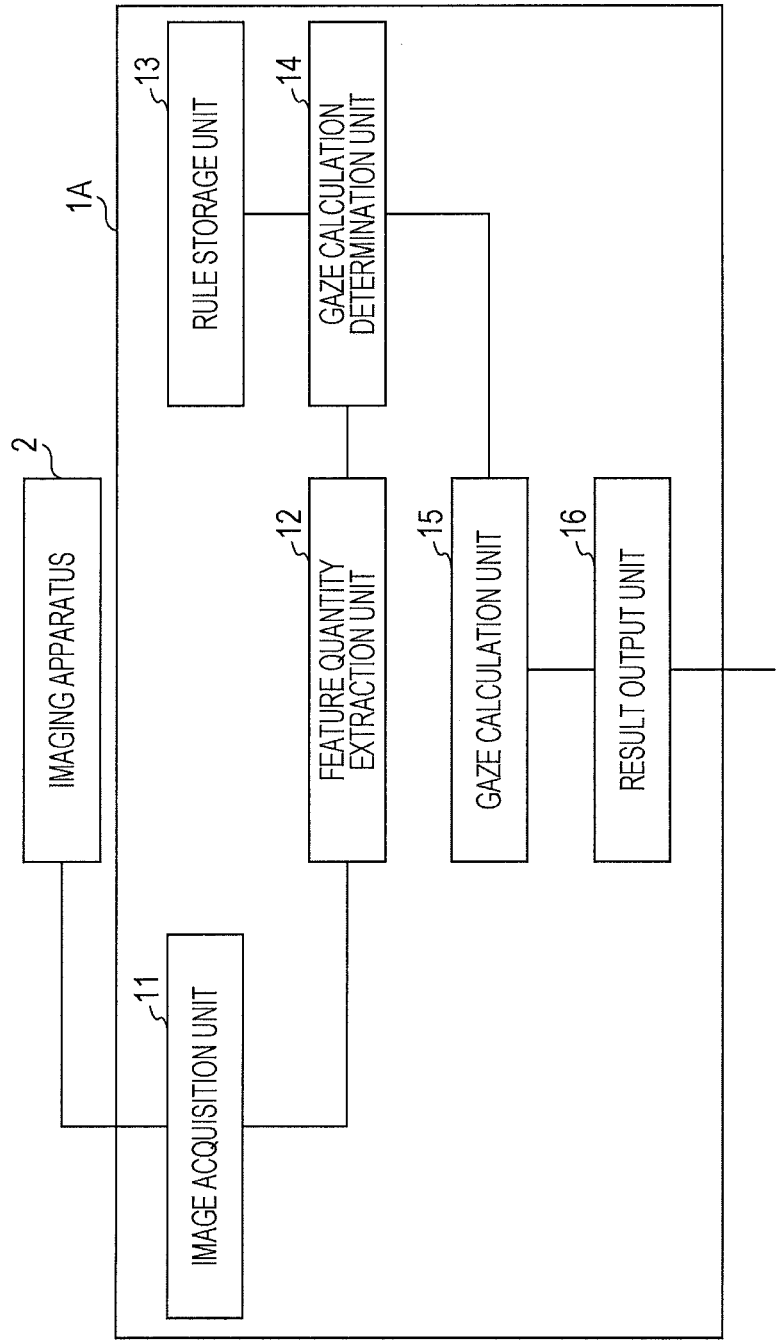
FIG. 1 is a diagram illustrating a functional configuration of an eye gaze detection apparatus according to this embodiment.

As described in the background, in the eye gaze detection technology of the related art it is assumed that a corneal reflection area is present in an image. In addition, in the eye gaze detection technology, there is the fact that a large load is applied to a calculator in order to calculate eye gazes such as a process for detecting a position of the iris from the captured image, a process for detecting a position of the pupil or the pupils from the position of the iris, and a process for specifying a position of eye gaze from a positional relationship with a position of the corneal reflection.

However, actually, the corneal reflection area is not present in the image in some cases, for example, at the time of closing an eye when performing the eye gaze calculation. Even in this case, a determining process of the corneal reflection area is performed in the eye gaze detection process of the related art. In addition, the captured image includes a frame in which a position of the eye gaze is not changed from a previous frame and a frame in which the position of eye gaze is not detectable. Even in this case, the eye gaze detection process is performed in the related art.

In other words, in the eye gaze detection technology of the related art, there is a problem in that even in a case where it is obviously not possible to perform the eye gaze detection, the eye gaze calculation process is performed, thereby performing a useless calculating process.

Accordingly, it is desired to provide an eye gaze detection apparatus, an eye gaze detection program, and an eye gaze detection method which are capable of efficiently performing a gaze detection process by reducing a processing load of the gaze detection process.

Hereinafter, description is given of the embodiments in detail with reference to the drawings. Generally, an eye gaze calculation process is performed to detect a user's eye gaze. Thus, the eye gaze calculation process is basically performed in all input images. However, in a state where the eye gaze calculation process is not able to be performed or the eye gaze calculation process is useless, the eye gaze calculation process is not desired.

Examples of the state where the eye gaze calculation process is not able to be performed include state where the user is blinking his or her eye (eye blink), a state where the user is closing his or her eye, a state where the user looking aside, a state where the user is cross-eyed, and a state where the user is looking sideways. In these cases, since information for the eye gaze calculation process, for example, a corneal reflection area which is used in a corneal reflection method is not present in an input image, it is not possible to perform the eye gaze calculation process. In addition, examples of the state where the eye gaze calculation process is not desired include a state where the user's eye remains stationary (focus), and the like. In this case, the same frames of the image for the eye gaze calculation process are consecutive, and thus the result of the eye gaze calculation process becomes the same. Therefore, performing the eye gaze calculation process is useless.

Thus, an image state is determined based on the feature quantity with respect to the eye gaze in the input image such as the candidate of the corneal reflection area. From this determination result, a target for the eye gaze calculation process is determined, and the eye gaze calculation process is performed on the target. By performing the eye gaze calculation process only when the eye gaze calculation process is desired, it is possible to reduce a processing load of a calculator when performing the eye gaze detection.

FIG. 1 is a diagram illustrating a functional configuration of an eye gaze detection apparatus according to the present embodiment. In FIG. 1, an eye gaze detection apparatus 1A is, for example, an information processing apparatus such as a work station, a personal computer, and a mobile communication terminal, and is connected to an imaging apparatus 2. The eye gaze detection apparatus 1A includes an image acquisition unit 11, a feature quantity extraction unit 12, a rule storage unit 13, an eye gaze calculation determination unit 14, an eye gaze calculation unit 15, and a result output unit 16.

The imaging apparatus 2 is, for example, a digital camera, a mobile phone with a camera, a surveillance camera, a video phone camera, or a web camera. Then, the imaging apparatus 2 captures, for example, a face image including a user's face and a face peripheral area.

The image acquisition unit 11 acquires the image of the user's face captured by the imaging apparatus 2 from the imaging apparatus 2 via a transmission path.

The feature quantity extraction unit 12 extracts the feature quantity of the face image acquired by the image acquisition unit 11. Here, the feature quantity represents, for example, a candidate of corneal reflection areas used in a corneal reflection method. The corneal reflection area is an area of reflection image in which the light incident on the eyeball is reflected on the corneal area.

The rule storage unit 13 stores a rule set as a rule database (refer to FIG. 7, FIG. 14, FIG. 18, and FIG. 23) which is described later. The rule database stores the rule set which associates a condition including the feature quantity of the face image with information indicating whether or not the eye gaze calculation process is performed.

For example, the rule database includes the rule set in which the eye gaze calculation process is not performed in a case where the feature quantity of the face image in a current frame coincides with the feature quantity of the face image in a previous frame at a predetermined ratio or higher. In addition, the rule database includes the rule set in which the eye gaze calculation process is not performed when the number of the feature quantities of the face image in the current frame is changed equal to or more than a predetermined number in comparison with the number of the feature quantities of the face image in the previous frame, and then the changed quantity of the changed feature quantity in a predetermined direction is within a predetermined value. Further, the rule database includes a rule set in which the eye gaze calculation process is not performed in a case where pixels on both sides of feature quantities in the right eye peripheral area and the left eye peripheral area are less than a predetermined number of white pixels. In addition, the rule database includes the rule set in which the eye gaze calculation process is not performed in a case where the size in the face area is smaller than a predetermined value. Further, the rule database includes the rule set in which the eye gaze calculation process is not performed in a case where the feature quantity is not extracted in the face area. The rule database includes the rule set in which the eye gaze calculation process is not performed in a case where the feature quantity in the face area is greater than a predetermined value. The rule database includes the rule set in which in a case where the feature quantities of the two face images are within an overlapped area of the two face images, the eye gaze calculation process is performed based on the feature quantity of any one of the face images.

The eye gaze calculation determination unit 14 determines whether or not to perform the user's eye gaze calculation process by referring to the rule database, based on the feature quantity extracted by the feature quantity extraction unit 12.

The eye gaze calculation unit 15 performs the user's eye gaze calculation process based on the feature quantity of the face image acquired by the image acquisition unit 11 when the eye gaze calculation determination unit 14 determines that the eye gaze calculation process is performed. The basic concept of the eye gaze calculation process is well known, for example, the eye gaze is calculated from the center of the corneal reflection area and the center of the pupil in the corneal reflection method.

The result output unit 16 outputs a result of the eye gaze calculation process which is performed by the eye gaze calculation unit 15.

Figure 2:
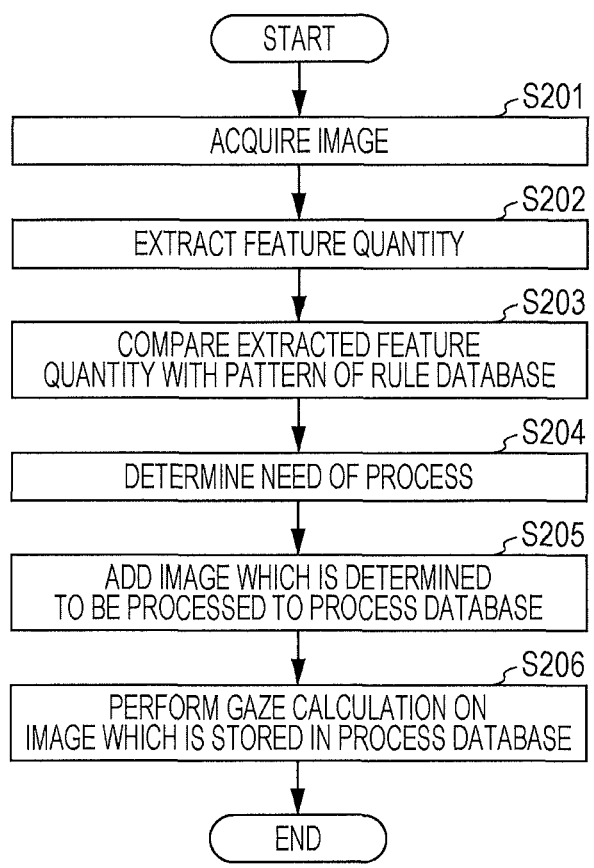
FIG. 2 is a flowchart illustrating a basic flow (part 1) of an eye gaze detection process performed by a computer of the eye gaze detection apparatus.

FIG. 2 is a flowchart illustrating a basic flow (part 1) of an eye gaze detection process performed by a computer of the eye gaze detection apparatus.

A flowchart illustrated in FIG. 2 illustrates a flow by so-called batch processing. First, in step S201, the image acquisition unit 11 acquires an image of a user's face captured by the imaging apparatus 2.

In step S202, the feature quantity extraction unit 12 extracts the feature quantity of the face image from the face image acquired in step S201.

In step S203, the eye gaze calculation determination unit 14 determines whether or not to perform the user's eye gaze calculation process in step S204 by referring to the rule database, based on the feature quantity extracted by the feature quantity extraction unit in step S202.

In addition, in step S205, the eye gaze calculation determination unit 14 stores the face image which is determined to be subject to the eye gaze calculation process in step S204 in a processing database described later (refer to FIGS. 11 and 20).

In step S206, the eye gaze calculation unit 15 performs the eye gaze calculation process based on the feature quantity of the face image which is acquired in step S201.

When a process in real time is not desired or when calibration is performed thereafter, the eye gaze detection process is performed by such batch processing.

Figure 3:
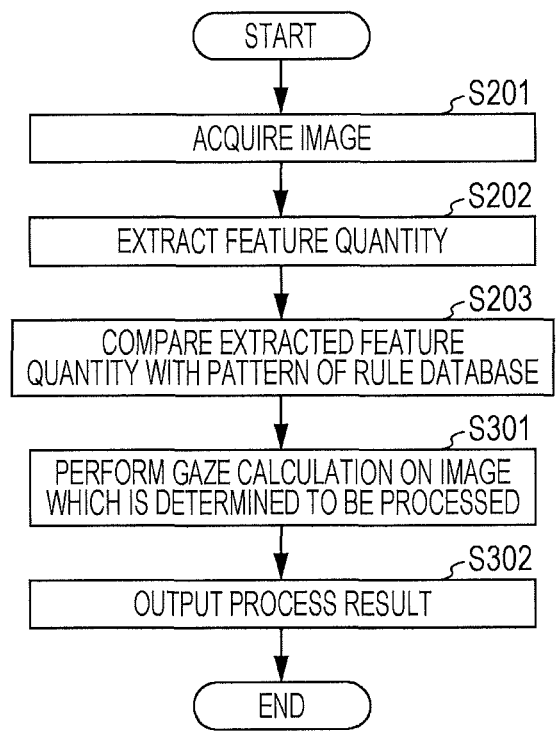
FIG. 3 is a flowchart illustrating a basic flow (part 2) of an eye gaze detection process performed by a computer of the eye gaze detection apparatus.

FIG. 3 is a flowchart illustrating a basic flow (part 2) of an eye gaze detection process performed by a computer of the eye gaze detection apparatus.

A flowchart illustrated in FIG. 3 illustrates a flow by so-called serial processing.

The description of step S201 to S203 is the same as that in the flowchart illustrated in FIG. 2, and thus will be omitted.

In step S301, the eye gaze calculation unit 15 performs the eye gaze calculation process based on the feature quantity of the face image which is determined to be subject to the eye gaze calculation process by the eye gaze calculation determination unit 14 in step S204.

In addition, in step S302, the result output unit 16 immediately outputs the result of the eye gaze calculation process which is performed in step S301.

It is possible to perform the eye gaze calculation in real time by performing the eye gaze detection process in such a serial processing.

Figure 4:
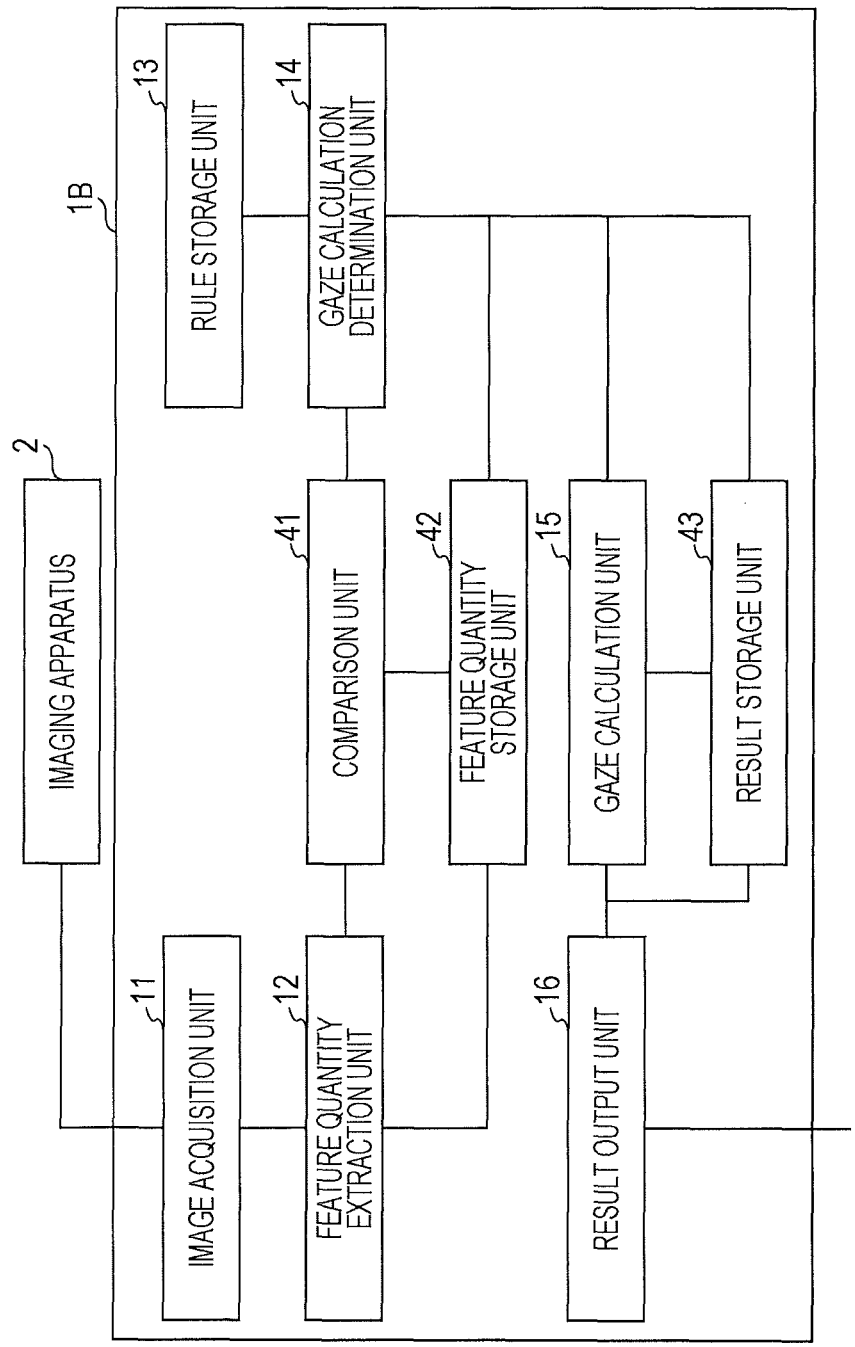
FIG. 4 is a diagram illustrating a functional configuration of an eye gaze detection apparatus according to a first embodiment.

FIG. 4 is a diagram illustrating a functional configuration of an eye gaze detection apparatus according to a first embodiment. In FIG. 4, the eye gaze detection apparatus 1B is, for example, an information processing apparatus such as a work station, a personal computer, and a mobile communication terminal, and is connected to the imaging apparatus 2. The eye gaze detection apparatus 1B includes an image acquisition unit 11, a feature quantity extraction unit 12, a comparison unit 41, a rule storage unit 13, an eye gaze calculation determination unit 14, a feature quantity storage unit 42, an eye gaze calculation unit 15, a result storage unit 43, and a result output unit 16.

The imaging apparatus 2 is, for example, a digital camera, and captures, for example, a user's face or a face image including a face peripheral area. Here, the face image may not include the entire user's face, and may include at least the user's eyes.

The image acquisition unit 11 acquires the image of user's face captured by the imaging apparatus 2 from the imaging apparatus 2 via the transmission path.

The feature quantity extraction unit 12 extracts the feature quantity of the face image acquired by the image acquisition unit 11, for example, the candidate of the corneal reflection area which is used in the corneal reflection method. Then, the extracted feature quantity is stored in the feature quantity storage unit 42.

The comparison unit 41 compares the feature quantity of the face image in the current frame with the feature quantity of the face image in the previous frame, which are extracted by the feature quantity extraction unit 12.

The rule storage unit 13 stores the rule set as the rule database. The rule database includes the rule set in which the eye gaze calculation process is not performed in a case where the feature quantity of the face image in the current frame coincides with the feature quantity of the face image in the previous frame at a predetermined ratio or higher. This rule set represents that the user's eye gaze remains stationary. In addition, the rule database includes the rule set in which the eye gaze calculation process is not performed when the number of the feature quantities of the face image in the current frame is changed equal to or more than a predetermined number in comparison with the number of the feature quantities of the face image in the previous frame, and then the changed quantity of the changed feature quantity in a predetermined direction is within a predetermined value. This rule set represents that the user is blinking his or her eye.

The eye gaze calculation determination unit 14 determines whether or not to perform the user's eye gaze calculation process by referring to the rule database, based on the feature quantity extracted by the feature quantity extraction unit 12. For example, the eye gaze calculation determination unit 14 determines that the eye gaze calculation process is not performed, based on a comparison result obtained by the comparison unit 41, in a case where the feature quantity of the face image in the current frame coincides with the feature quantity of the face image in the previous frame equal to or greater than a predetermined ratio. In addition, the eye gaze calculation determination unit 14 determines that the eye gaze calculation process is not performed, based on a comparison result obtained by the comparison unit 41, when the number of the feature quantities of the face image in the current frame is changed equal to or more than a predetermined number in comparison with the number of the feature quantities of the face image in the previous frame, and then the changed quantity of the changed feature quantity in a predetermined direction is within a predetermined value.

The feature quantity storage unit 42 stores the feature quantity of the face image extracted by the feature quantity extraction unit 12 when the eye gaze calculation determination unit 14 determines that the eye gaze calculation process is performed.

The eye gaze calculation unit 15 performs the user's eye gaze calculation process, based on the feature quantity of the face image acquired by the image acquisition unit 11, when the eye gaze calculation determination unit 14 determines that the eye gaze calculation process is performed. For example, the eye gaze is calculated from the center of the corneal reflection area and the center of the pupil in the corneal reflection method.

The result storage unit 43 stores coordinates of an eye gaze point, an eye gaze vector, or the like based on a result of the eye gaze calculation process performed by the eye gaze calculation unit 15. This is to output the stored result of the previous frame when the user's eyes are determined to remain stationary. The result output unit 16 outputs the result of the eye gaze calculation process which is performed by the eye gaze calculation unit 15.

Figure 5A:
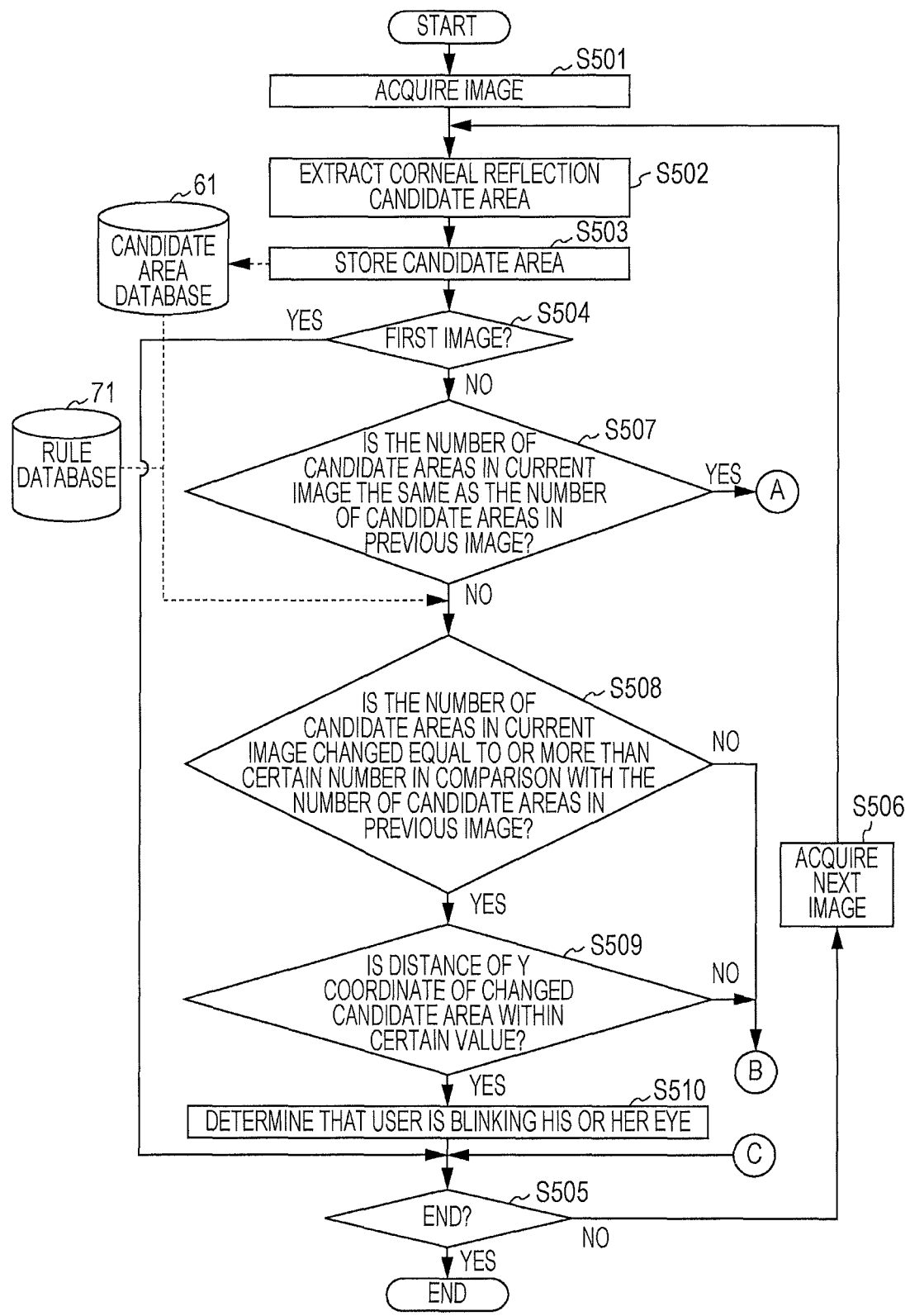
FIGS. 5A and 5B are flowcharts illustrating an eye gaze detection process by serial processing performed by a computer of an eye gaze detection apparatus according to the first embodiment.
Figure 5B:
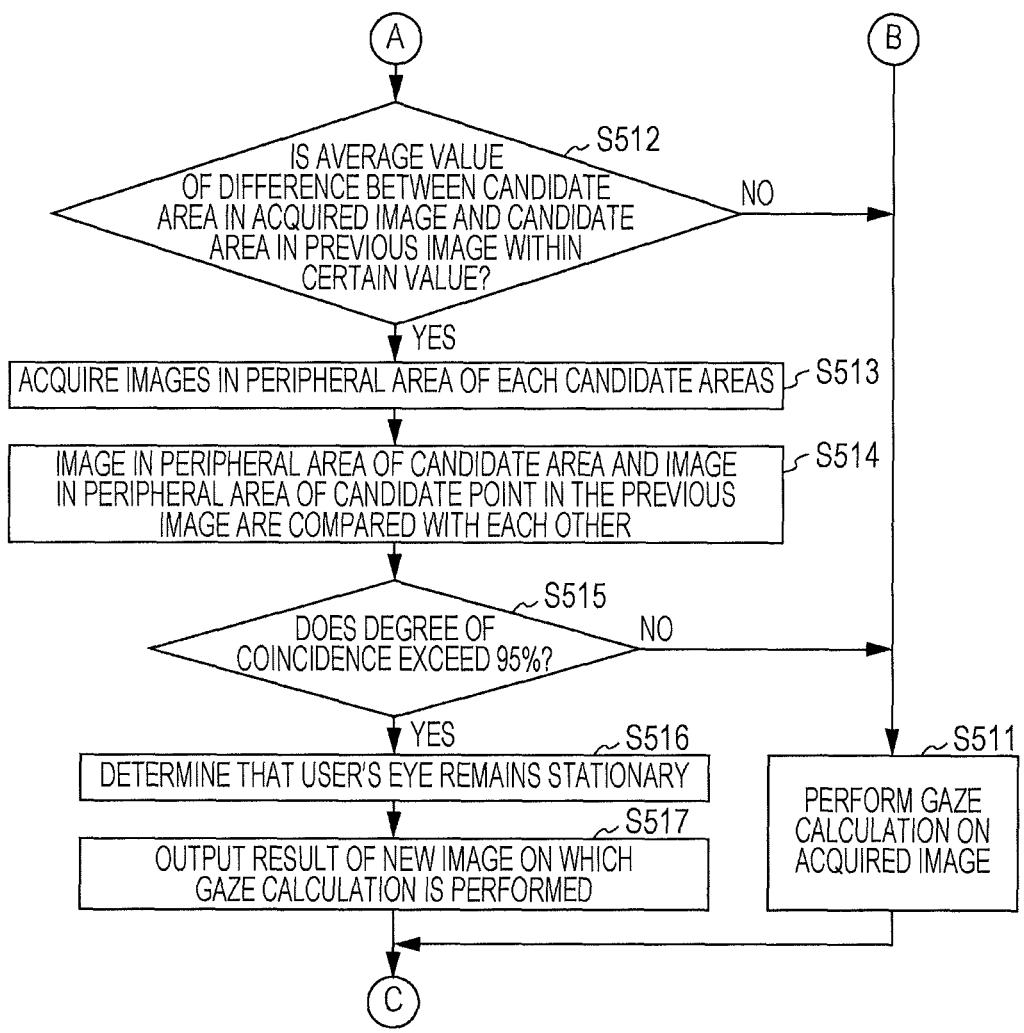
Figure 9A:
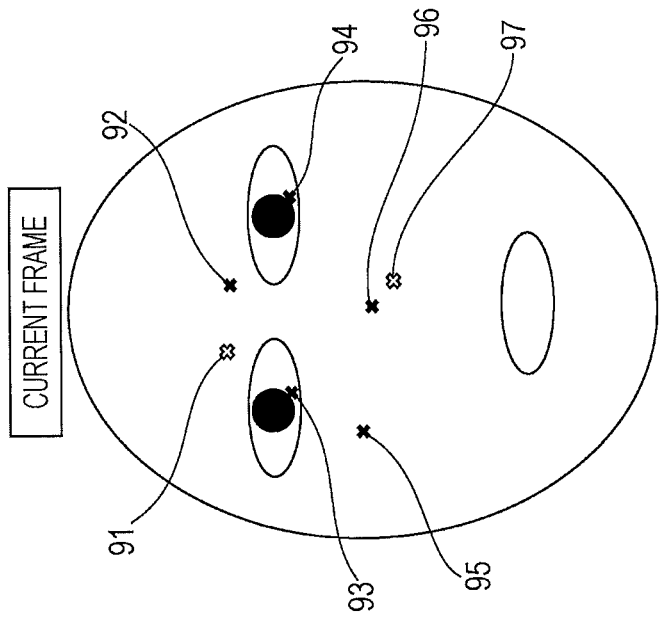
FIGS. 9A and 9B are diagrams illustrating an example of a face image when it is determined that the user is not blinking his or her eye.
Figure 9B:
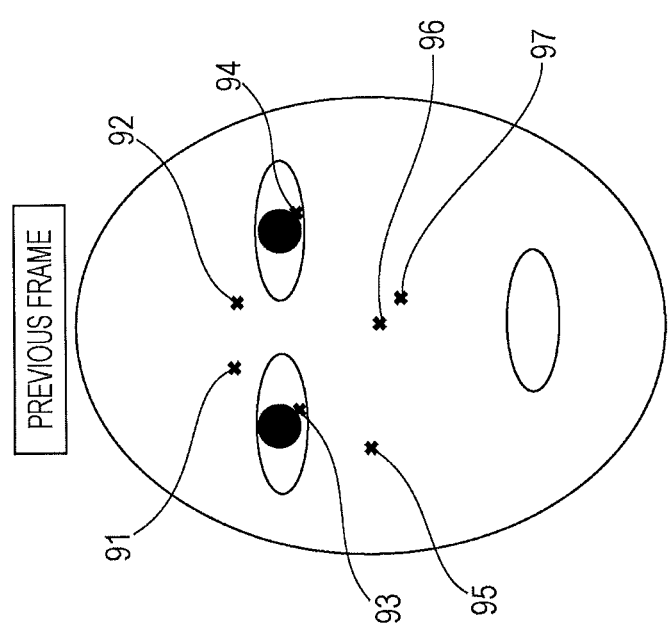

FIGS. 5A and 5B are flowchart illustrating an eye gaze detection process by serial processing performed by a computer of an eye gaze detection apparatus according to the first embodiment. FIG. 6 is a diagram illustrating an example of a candidate area database. FIG. 7 is a diagram illustrating an example of a rule database (part 1). FIGS. 8A and 8B are diagrams illustrating examples of a face image when it is determined that a user is blinking his or her eye. FIGS. 9A and 9B are diagrams illustrating examples of a face image when it is determined that the user is not blinking his or her eye.

Flowcharts illustrated in FIGS. 5A and 5B illustrate a flow of the eye gaze detection process in a case where the eye gaze calculation process is performed only when the eye gaze calculation process is desired, by determining a state where the user is blinking his or her eye or the user's eye remains stationary as the state where the eye gaze calculation process is not able to be performed. Determination criteria are stored in the rule database in advance. The above described eye gaze detection apparatus 1B is realized by the aforementioned information processing apparatus which performs the eye gaze detection process as below.

First, in step S501 of FIG. 5A, the image acquisition unit 11 acquires the image of a user's face captured by the imaging apparatus 2 from the imaging apparatus 2 via the transmission path.

In step S502, the feature quantity extraction unit 12 extracts the candidate of the corneal reflection area as the feature quantity of the face image acquired by the image acquisition unit 11. The candidate of the corneal reflection area is a high luminance area in the face image, and may be extracted through a binarization process, a filtering process, a template matching process, a corner detection process, or the like. In addition, in step S503, the extracted candidate of the corneal reflection area is stored in the feature quantity storage unit 42 as a candidate area database 61 as illustrated in FIG. 6. The candidate area database 61 in FIG. 6 stores, for example, coordinates (10, 10), (10, 12), (100, 14), (100, 12), and (100, 15) in the face image which is captured at "00:00:01.033", is stored as the candidate of the corneal reflection area.

In step S504, it is determined whether or not the face image acquired in step S501 is the first image.

Since the face image acquired in step S501 is the first image (step S504: Yes), it is determined whether or not to end the current eye gaze detection process in step S505. Unless there is an instruction to end from the outside, normally, the current eye gaze detection process does not end.

When the process does not end (step S505: No), the next face image is acquired in step S506.

Then, in step S502, the feature quantity extraction unit 12 extracts the candidate of the corneal reflection area from the next face image which is acquired in step S506, and in step S503, the extracted candidate of the corneal reflection area is stored in the candidate area database 61 as illustrated in FIG. 6.

In addition, in step S504, it is determined again whether or not the face image acquired in step S506 is the first image.

Since the face image acquired in step S506 is not the first image (step S504: No), in step S507, the eye gaze calculation determination unit 14 refers to the rule database 71 as illustrated in FIG. 7, and the comparison unit 41 compares the number of candidates of the corneal reflection area of the face image in the current frame with the number of candidates of the corneal reflection area of the face image in the previous frame.

As a result of the comparison, when the number of candidates of the corneal reflection area is not the same as each other (step S507: No), in step S508, it is determined whether or not the changed number of candidates of the corneal reflection area is equal to or more than a certain number, for example, equal to or more than two. In addition, when the number is changed equal to or more than a certain number (step S508: Yes), in step S509, it is determined whether or not y coordinate values of the changed candidate of the corneal reflection area, that is, coordinate values in the vertical direction of the face image are within a certain range. When y coordinate values are within a certain range (step S509: Yes), in step S510, the eye gaze calculation determination unit 14 determines that the user is blinking his or her eye as illustrated in FIGS. 8A and 8B. That is, when the number of the corneal reflection is reduced equal to or more than a certain number in comparison with the number of the corneal reflection of the face image in the previous frame, the frame is determined in which the user is blinking his or her eye. The fact that an eyelid covers a part of the iris, and thus the corneal reflection which is generated in the part of the iris is reduced is used to support the above determination.

For example, seven candidates of the corneal reflection area 81, 82, 83, 84, 85, 86, and 87 in the previous frame are extracted in FIG. 8A. Five candidates of the corneal reflection area 81, 82, 85, 86, and 87 in the current frame are extracted in FIG. 8B. Two candidates of the corneal reflection area 83 and 84 are not extracted in the current frame as the candidate of the corneal reflection area. That is, in the examples illustrated in FIGS. 8A and 8B, in step S507, the number of candidates of the corneal reflection area is not the same as each other (step S507: No). In step S508, it is determined that two or more candidates of the corneal reflection area are changed (step S508: Yes). In step S509, it is determined that the y coordinate values of the changed candidates of the corneal reflection area 83 and 84 are within a certain range (step S509: Yes). In this case, the changed candidates of the corneal reflection area 83 and 84 are the corneal reflection areas, and are considered to be changed by the user blinking his or her eye.

In addition, seven candidates of the corneal reflection area 91, 92, 93, 94, 95, 96, and 97 in the previous frame are extracted in FIG. 9A. Five candidates of the corneal reflection area 92, 93, 94, 95, and 96 in the current frame are extracted in FIG. 9B. Two candidates of the corneal reflection area 91 and 97 are not extracted in the current frame as the candidate of the corneal reflection area. That is, in the examples illustrated in FIGS. 9A and 9B, in step S507, the number of candidates of the corneal reflection area is not the same as each other (step S507: No). In step S508, it is determined that two or more candidates of the corneal reflection area are changed (step S508: Yes). In step S509, it is determined that the y coordinate values of the changed candidates of the corneal reflection area 91 and 97 are not within a certain range (step S509: No).

In addition, when it is determined that the y coordinate values of the changed candidates of the corneal reflection area are not within a certain range (step S509: No), as usual, in step S511, the eye gaze calculation unit 15 performs the eye gaze calculation process based on the feature quantity of the face image which is acquired in step S506. Even when it is determined that two or more candidates of the corneal reflection area are not changed (step S508: No) in step S508, in step S511, the eye gaze calculation unit 15 performs the eye gaze calculation process based on the feature quantity of the face image which is acquired in step S506.

On the other hand, when it is determined that the number of candidates of the corneal reflection area of the face image in the current frame is the same as the number of candidates of the corneal reflection area of the face image in the previous frame in step S507 (step S507: Yes), in step S512, it is determined that whether or not an average value of a difference between the coordinate value of the candidates of the corneal reflection area corresponding to the face image in the current frame and the coordinate value of the candidates of the corneal reflection area corresponding to the face image in the previous frame is within a certain value.

When the average value is not within a certain value (step S512: No), since it is considered that a position of the candidate of the corneal reflection area corresponding to the face image in the current frame is different from a position of the candidate of the corneal reflection area corresponding to the face image in the previous frame, the process proceeds to step S511.

On the other hand when the average value is within a certain value (step S512: Yes), images in the peripheral area of the candidates of the corneal reflection area of the face image in the current frame and the previous frame are acquired in step S513. In step S514, the peripheral area corresponding to the face image in the current frame and the peripheral area corresponding to the face image in the previous frame are compared with each other. Then, in step S515, the eye gaze calculation determination unit 14 determines whether or not the degree of coincidence exceeds 95%.

When the degree of coincidence does not exceed 95% (step S515: No), the process proceeds to step S511. On the other hand, when the degree of coincidence exceeds 95% (step S515: Yes), in step S516, the eye gaze calculation determination unit 14 determines that the user's eye remains stationary. That is, it is determined that a position of the eye gaze is not changed when the change of the position is within a predetermined value when specifying the position of the iris and comparing the position of the iris in the current frame with the position of the iris in the previous frame.

Then, in step S517, the result output unit 16 outputs the result of the eye gaze detection process.

In this way, when it is considered that the position of the eye gaze of the face image which is subjected to the eye gaze calculation process is not changed compared with the position of the eye gaze of the face image in the previously captured frame, or when satisfying conditions which determines that the eye gaze calculation process from the face image is not performed, the corresponding face image is removed from the targets for the eye gaze calculation process.

Meanwhile, determination of the state where the user's eye remains stationary or the state where the user is blinking his or her eye is obtained from the difference between the candidates of the corneal reflection area in the current frame and the candidates of the corneal reflection area in the previous frame; however, another method may be used. For example, when the use's eye remains stationary, a method such as a pattern matching of an iris may be used. In addition, when the user is blinking his or her eye, a method of using a motion vector, or a technology for detecting and tracing an eye or an eye blink from the image of a user's face may be used (for example, refer to Japanese Laid-open Patent Publication No. 2001-43382).

In addition, it is possible to perform the same eye gaze detection process with respect to each of a plurality of users by additionally performing the face detection process.

Figure 10A:
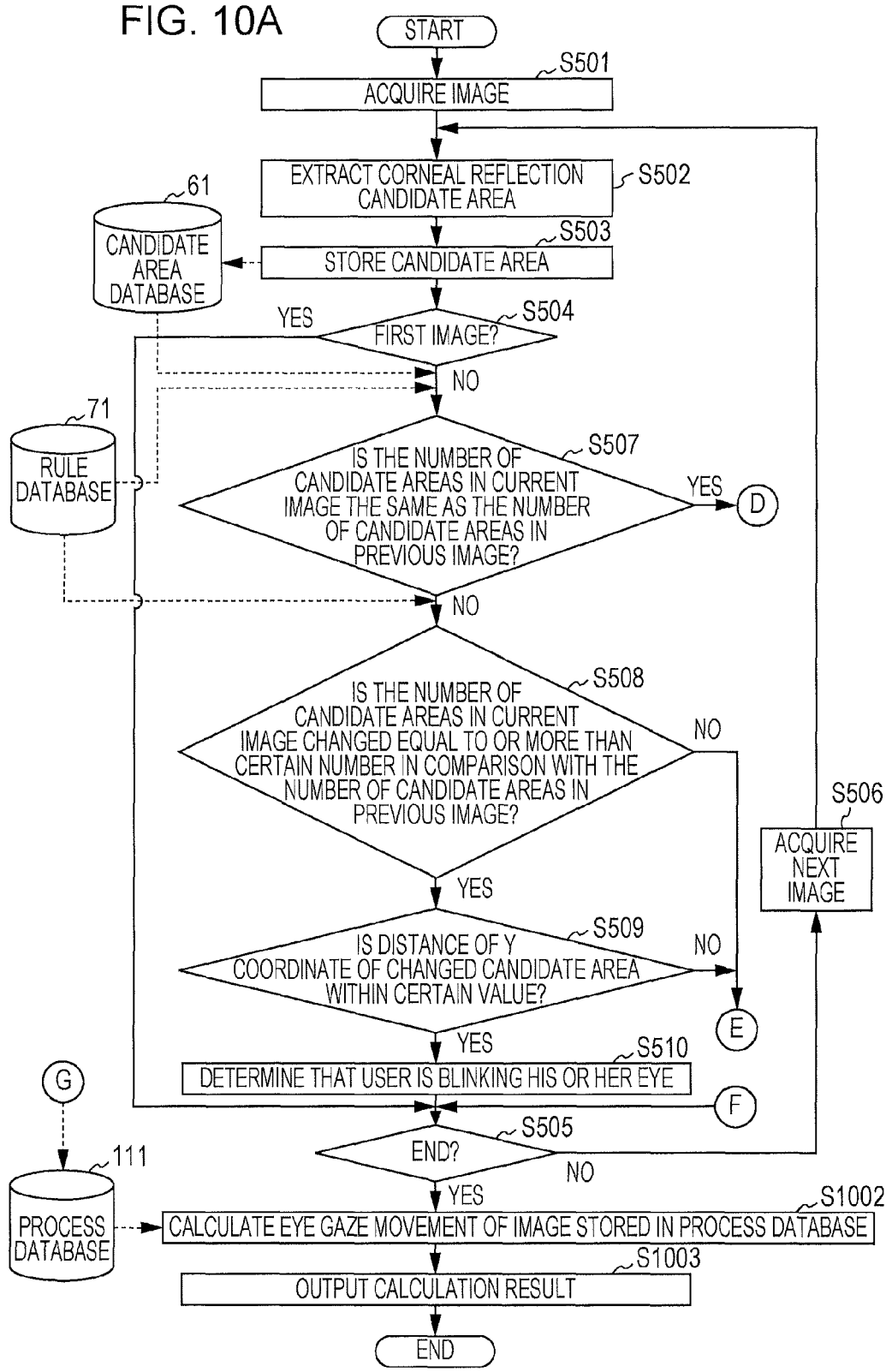
FIGS. 10A and 10B are flowcharts illustrating a flow of the eye gaze detection process by batch processing performed by the computer of the eye gaze detection apparatus according to a second embodiment.
Figure 10B:
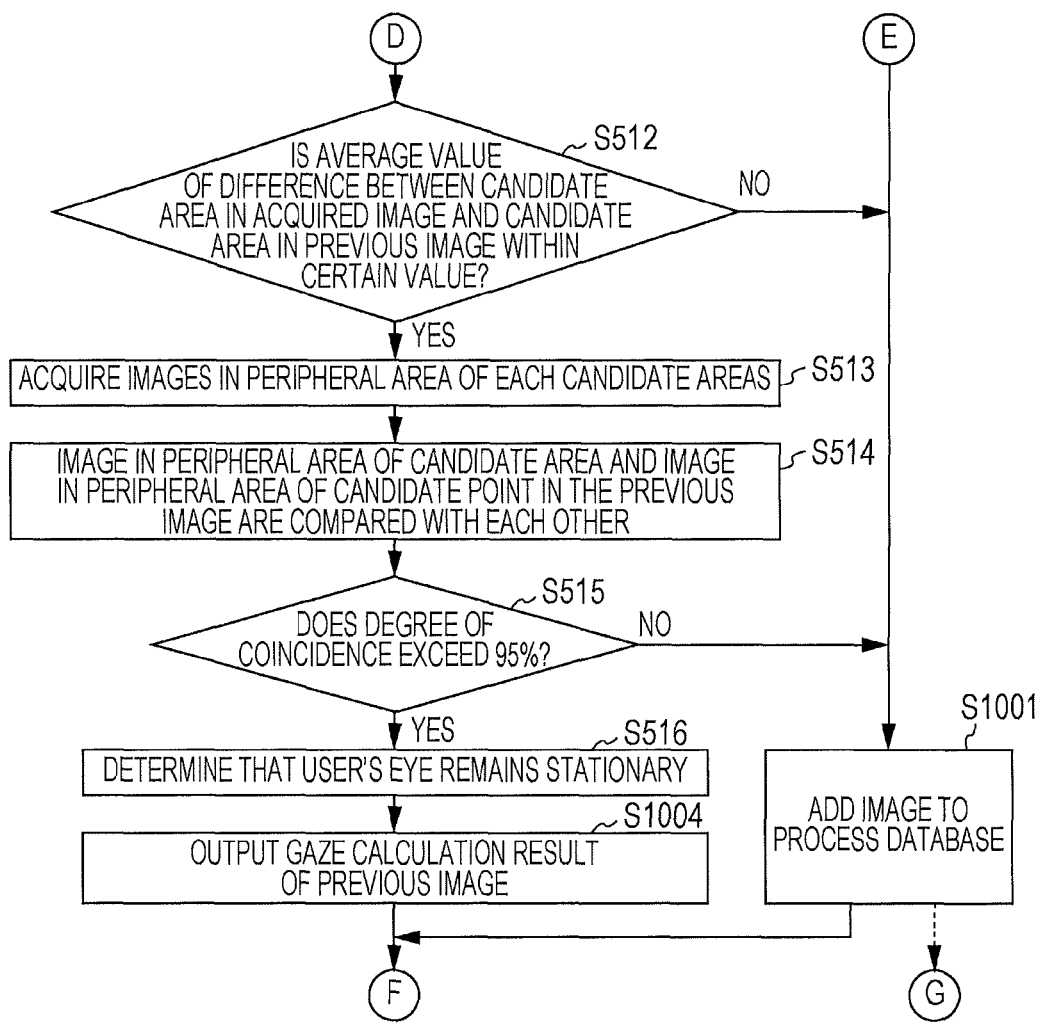

FIGS. 10A and 10B are flowcharts illustrating a flow of the eye gaze detection process by batch processing performed by the computer of the eye gaze detection apparatus according to the second embodiment. FIG. 11 is a diagram illustrating an example of a processing database (part 1).

Description is given of steps which are different from the steps of the eye gaze detection process by the serial processing performed by the computer of the eye gaze detection apparatus according to the first embodiment as illustrated in FIGS. 5A and 5B.

Steps S501 to S510 and steps S512 to S516 are the same as the steps of the eye gaze detection process by the serial processing performed by the computer of the eye gaze detection apparatus according to the first embodiment as illustrated in FIGS. 5A and 5B. That is, the second embodiment is the same as the first embodiment regarding a point in that the acquisition of the face image, the feature quantity extraction, the determination of the user's eye blinking, and the determination of the user's eye remaining stationary. The determination criteria are stored in the rule database in advance.

In step S508, when it is determined that the number of candidates of the corneal reflection area of the face image in the current frame and the number of candidates of the corneal reflection area of the face image in the previous frame are not changed equal to or more than two (step S508: No), the face image acquired in step S506 is stored in processing database 111 as illustrated in FIG. 11 in step S1001. In the processing database 111 in FIG. 11, for example, the face image which is captured at time "00:00: 00.033" is stored as a frame 1. This face image is used to perform the eye gaze calculation process later.

in addition, in step S509, when the y coordinate values of the changed candidates of the corneal reflection area are not within a certain range (step S509: No), the face image acquired in step S506 is stored in the processing database 111 in step S1001. In addition, the face image acquired in step S506 is stored in the processing database 111 in step S1001 in a case where the average value of the difference between the coordinate value of the candidates of the corneal reflection area corresponding to the face image in the current frame and the coordinate value of the candidates of the corneal reflection area corresponding to the face image in the previous frame is not within a certain value in step S512 (step S512: No) and also in a case where the degree of coincidence between the peripheral area corresponding to the face image in the current frame and the peripheral area corresponding to the face image in the previous frame does not exceed 95% in step S515 (step S515: No).

When it is determined to end the present eye gaze detection process (step S505: Yes), in step S1002, the eye gaze calculation unit 15 performs the eye gaze calculation process based on the feature quantity of the face image stored in the processing database 111 in step S1001.

Then, in step S1003, the result output unit 16 outputs the result of the eye gaze detection process performed in step S1002.

Figure 12:
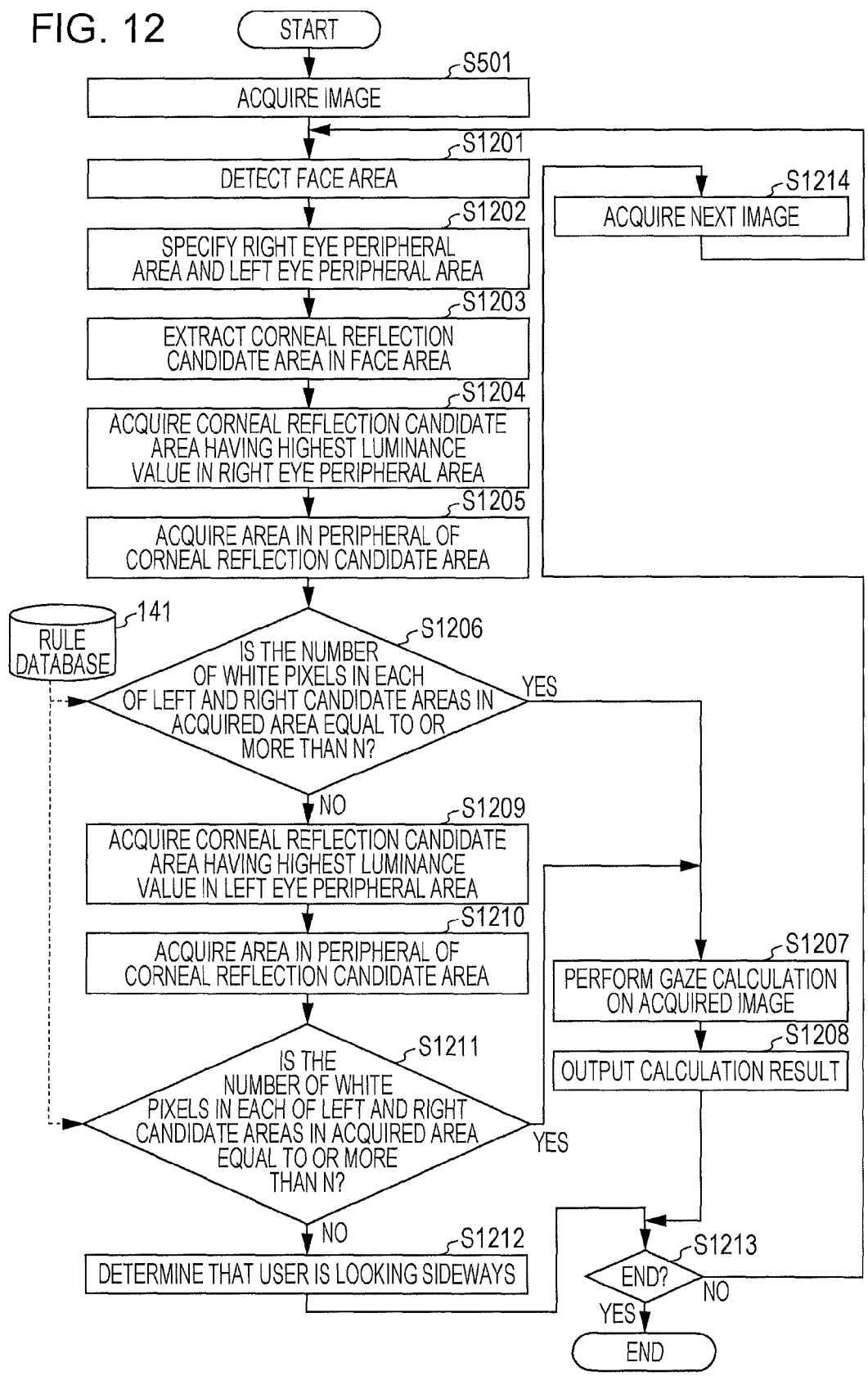
FIG. 12 is a flowchart illustrating an eye gaze detection process by serial processing performed by a computer of an eye gaze detection apparatus according to a third embodiment.
Figure 13:
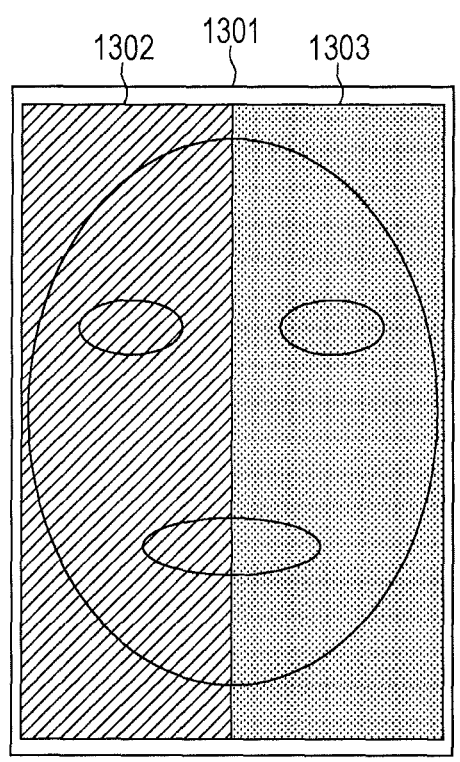
FIG. 13 is a diagram illustrating a right eye peripheral area and a left eye peripheral area of a face image.
Figure 15:
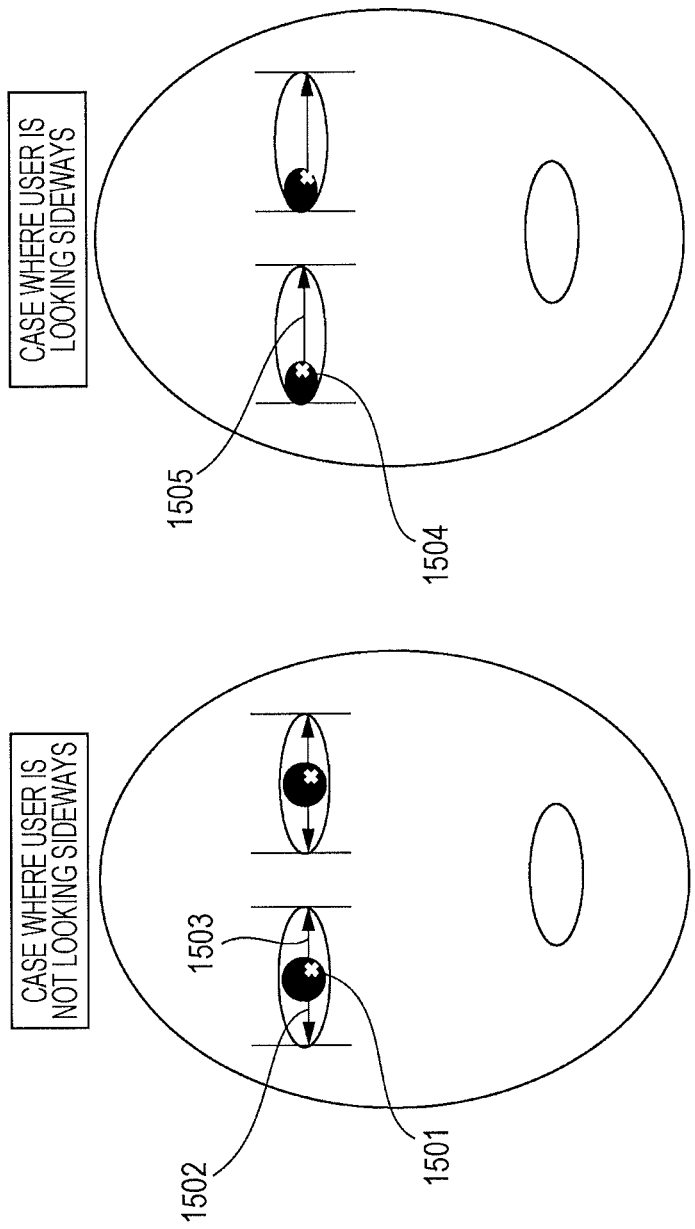
FIGS. 15A and 15B are diagrams illustrating examples of the face image in which it is determined that the user is looking sideways.

FIG. 12 is a flowchart illustrating the eye gaze detection process by the serial processing performed by a computer of an eye gaze detection apparatus according to a third embodiment. FIG. 13 is a diagram illustrating a right eye peripheral area and a left eye peripheral area of the face image. FIG. 14 is a diagram illustrating an example of a rule database (part 2). FIG. 15 is a diagram illustrating an example of the face image which is determined that the user is looking sideways.

A flowchart illustrated in FIG. 12 illustrates a flow of the eye gaze detection process in a case where the eye gaze calculation process is performed only when the eye gaze calculation process is desired, by determining a state where the user is looking sideways as the state where the eye gaze calculation process is not able to be performed. Since it is difficult to accurately obtain the shape of the iris in the state where the user is looking sideways and thus a large error is generated, the eye gaze calculation process is not desired.

The eye gaze detection process according to the third embodiment determines whether or not to perform the eye gaze calculation process by using information of the area of corneal reflection candidate and the face area. The determination criteria are stored in the rule database in advance. In addition, it is considered that known technology is used as a process for detecting the face area from the input face image. For example, A technology for extracting a partial image which is considered to include a face image based on an edge image extracted from a target image, and determining whether or not the extracted partial image includes the face image by referring a learning dictionary that holds learning information for identifying the face image and a non-face image (for example, refer to Japanese Laid-open Patent Publication No. 2003-44853). Note that the face area may be an area including a face or a part of face such as an eye.

First, in step S501 of FIG. 12, the image acquisition unit 11 acquires the image of user's face captured by the imaging apparatus 2 from the imaging apparatus 2 via the transmission path. In step S1201, the image acquisition unit 11 performs detection in a face area 1301 from the acquired face image as illustrated in FIG. 13. Then, in step S1202, the image acquisition unit 11 specifies a right eye peripheral area 1302 and a left eye peripheral area 1303, which are within a predetermined range, from the detected face area 1301 as illustrated in FIG. 13. The right eye peripheral area 1302 includes an image of the right eye and the left eye peripheral area 1303 includes an image of the left eye.

In step S1203, the feature quantity extraction unit 12 extracts the candidate of the corneal reflection area as the feature quantity in the face area 1301 which is detected by the image acquisition unit 11.

Next, in step S1204, among the candidates of the corneal reflection area which are extracted in step S1203, the feature quantity extraction unit 12 acquires one candidate of the corneal reflection area, which is in the right eye peripheral area 1302 specified in step S1202 and has the highest luminance value. For example, when expressing the area from a black pixel to the white pixel by 8 bits (256 gradations), the luminance value which is equal to or greater than 240 is the highest luminance value in many cases. Having the highest possibility of the corneal reflection area, the candidate of the corneal reflection area having the highest luminance value is acquired. In step S1205, the feature quantity extraction unit 12 acquires the peripheral area of the candidate of the corneal reflection area having the highest luminance value among the right eye peripheral area 1302, that is, a corneal peripheral area image having the highest possibility of the corneal reflection area.

In step S1206, the eye gaze calculation determination unit 14 refers to the rule database 141 as illustrated in FIG. 14. Then, it is determined whether or not pixels on both sides of the candidate of the corneal reflection area (horizontal direction: an X axial direction) are equal to or more than a predetermined number of white pixels (for example, a predetermined number of n) in the corneal peripheral area image which is acquired in step S1205. Here, when expressing the area from the black pixel to the white pixel by 8 bits (256 gradations), it is preferable that the white pixel has the luminance value in a range of 190 to 230.

In a case where the left and right pixels of the candidate of the corneal reflection area are a predetermined number or more of the white pixels (step S1206: Yes), the eye gaze calculation determination unit 14 determines that the user is not looking sideways, and the eye gaze calculation unit 15 performs the eye gaze calculation process based on the feature quantity of the face image in step S1207. Then, in step S1208, the result output unit 16 outputs the result of the performed eye gaze detection process. For example, as illustrated in FIG. 15A, on both sides of the candidate of the corneal reflection area having the highest luminance value 1501 the white pixels 1502 and 1503 which are equal to or greater than a predetermined number.

On the other hand, in a case where the left and right pixels of the candidate of the corneal reflection area are not a predetermined number or more of the white pixels in step S1206 (step S1206: No), the eye gaze calculation determination unit 14 determines there is a possibility that the user is looking sideways. For example, as illustrated in FIG. 15B, a predetermined number or more of the white pixels 1505 are present only on the one side of the candidate of the corneal reflection area having the highest luminance value 1504.

Then, in step S1209, the feature quantity extraction unit 12 acquires one candidate of the corneal reflection area having the highest luminance value in the left eye peripheral area 1303 which is specified in step S1202, among the candidates of the corneal reflection area extracted in step S1203. In step S1210, the feature quantity extraction unit 12 acquires the peripheral area of the candidate of the corneal reflection area having the highest luminance value among the left eye peripheral area 1303, that is, the corneal peripheral area image having the highest possibility of the corneal reflection area.

In step S1211, the eye gaze calculation determination unit 14 refers to the rule database 141 as illustrated in FIG. 14. Then, it is determined whether or not pixels on both sides of the candidate of the corneal reflection area (horizontal direction: the X axial direction) are equal to or more than a predetermined number of white pixels (for example, a predetermined number of n) in the corneal peripheral area image which is acquired in step S1210.

In a case where the left and right pixels of the candidate of the corneal reflection area are a predetermined number or more of the white pixels (step S1211: Yes), the eye gaze calculation determination unit 14 determines that the user is not looking sideways, and the eye gaze calculation unit 15 performs the eye gaze calculation process based on the feature quantity of the face image in step S1207. Then, in step S1208, the result output unit 16 outputs the result of the performed eye gaze detection process.

On the other hand, in a case where the left and right pixels of the candidate of the corneal reflection area are not a predetermined number or more of the white pixels in step S1211 (step S1211: No), the eye gaze calculation determination unit 14 determines that the user is looking sideways in step S1212.

Then, in step S1213, it is determined whether or not to end the current eye gaze detection process. Unless there is an instruction to end from the outside, normally, the current eye gaze detection process does not end. When the process does not end (step S1213: No), the next face image is acquired in step S1214.

As described above, in the eye gaze detection process according to the third embodiment, it is determined whether or not a high luminance area (white of an eye) in a predetermined range on both sides of the position of the corneal reflection area (the horizontal direction), and then when the high luminance area is present on only one side, it is determined that the user is looking sideways. Meanwhile, the same is true for a case where the user is cross-eyed.

Figure 16:
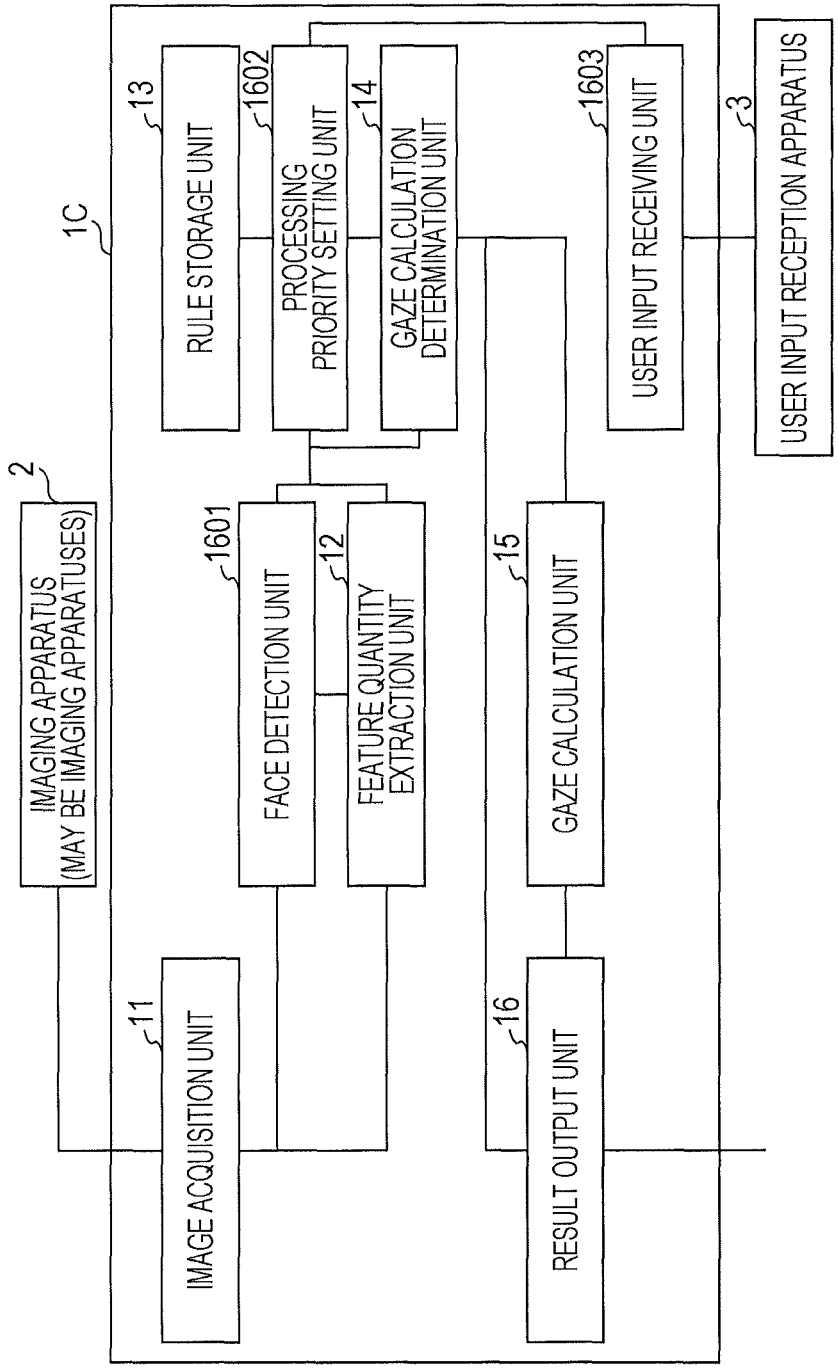
FIG. 16 is a diagram illustrating a functional configuration of an eye gaze detection apparatus according to fourth to eighth embodiments.

FIG. 16 is a diagram illustrating a functional configuration of an eye gaze detection apparatus according to fourth to eighth embodiments.

In FIG. 16, an eye gaze detection apparatus 1C is, for example, an information processing apparatus such as a workstation, a personal computer, and a portable communication terminal, and is connected to the imaging apparatus 2 and an input reception device 3. The eye gaze detection apparatus 1C includes the image acquisition unit 11, a face detection unit 1601, the feature quantity extraction unit 12, the rule storage unit 13, a processing priority setting unit 1602, the eye gaze calculation determination unit 14, the eye gaze calculation unit 15, the result output unit 16, and a user input receiving unit 1603.

The imaging apparatus 2 is, for example, a digital camera and the like, and captures, for example, a face image including a user's face and a face peripheral area. The imaging apparatus 2 may be configured to include a plurality of cameras.

The input reception device 3 is an input device such as a keyboard, or a mouse, and the user inputs a processing priority setting by using the input reception device.

The image acquisition unit 11 acquires the image of user's face captured by the imaging apparatus 2 from the imaging apparatus 2 via the transmission path. In a case where the imaging apparatus 2 is configured to include the plurality of cameras, the image acquisition unit 11 acquires the face images captured by each imaging apparatus 2 from each imaging apparatus 2.

The face detection unit 1601 detects the face area from the face image acquired by the image acquisition unit 11. For example, the face area is detected from the face image by extracting a partial image which is considered to include a face image based on an edge image extracted from a target image, referring a learning dictionary for identifying the face image and a non-face image, and then determining whether or not the extracted partial image includes the face image.

The feature quantity extraction unit 12 extracts the feature quantity of the face image acquired by the image acquisition unit 11, for example, the candidate of the corneal reflection area which is used in the corneal reflection method. In addition, the feature quantity extraction unit 12 extracts the feature quantity in the face area which is detected by the face detection unit 1601. In a case where the imaging apparatus 2 is configured to include a plurality of cameras, the feature quantity extraction unit 12 extracts the feature quantity of the face image acquired from the respective cameras. Then, the extracted feature quantity is stored in the feature quantity storage unit 42.

The rule storage unit 13 stores the rule set as the rule database. The rule database includes the rule set in which the eye gaze calculation process is not performed in a case where the size in the face area is smaller than a predetermined value. This rule set represents that since the user's face captured by the imaging apparatus 2 is too small, it is not possible to perform the eye gaze detection. In addition, the rule database includes the rule set in which the eye gaze calculation process is not performed in a case where the extracted feature quantity is extracted in an area other than the face area and the feature quantity is not extracted in the face area. This rule set represents that since the feature quantity is detected by metal or the like in an area other than the face area, it is not possible to perform the eye gaze detection. In addition, the rule database includes the rule set in which the eye gaze calculation process is not performed in a case where the feature quantity in the face area is greater than a predetermined value. This rule set represents that since the feature quantity in the face area is obtained by reflection with the glasses or the like, it is not possible to perform the eye gaze detection. Further, the rule database includes the rule set in which in a case where the feature quantities of the two face images are within an overlapped area of the two face images, the eye gaze calculation process is performed based on the feature quantity of any one of the face images. This rule set represents that there is a high possibility of obtaining the same result of the eye gaze calculation based on the feature quantities of both of the face images, and thus the eye gaze detection of one side may be sufficient.

The processing priority setting unit 1602 associates the feature quantity in the face area extracted by the feature quantity extraction unit 12 with a priority of performing the eye gaze calculation process, and then stores the set priority in the processing database.

The eye gaze calculation determination unit 14 determines whether or not to perform the user's eye gaze calculation process by referring the rule database, based on the feature quantity extracted by the feature quantity extraction unit 12. For example, the eye gaze calculation determination unit 14 determines that the eye gaze calculation process is not performed in a case where the size in the face area which is detected by the face detection unit 1601 is smaller than a predetermined value. In addition, the eye gaze calculation determination unit 14 determines that the eye gaze calculation process is not performed in a case where the feature quantity which is extracted by the feature quantity extraction unit 12 is extracted from an area other than the face area and the feature quantity is not extracted in the face area. In addition, the eye gaze calculation determination unit 14 determines that eye gaze calculation process is not performed in a case where the size of feature quantity in the face area which is extracted by the feature quantity extraction unit 12 is greater than a predetermined value. In addition, the eye gaze calculation determination unit 14 determines that the eye gaze calculation process is performed according to the priority of the feature quantity in the face area extracted by the feature quantity extraction unit 12. Further, the eye gaze calculation determination unit 14 determines that the eye gaze calculation process is performed based on the feature quantity of any one of the face images in a case where feature quantities of the plurality of face images which are extracted by the feature quantity extraction unit 12 are in an overlapped area of the plurality of face images which are acquired by the image acquisition unit 11.

The eye gaze calculation unit 15 performs the user's eye gaze calculation process, based on the feature quantity of the face image acquired by the image acquisition unit 11, when the eye gaze calculation determination unit 14 determines that the eye gaze calculation process is performed. For example, the eye gaze is calculated from the center of the corneal reflection area and the center of the pupil in the corneal reflection method.

The result output unit 16 outputs the result of the eye gaze calculation process which is performed by the eye gaze calculation unit 15.

The user input receiving unit 1603 receives the processing priority setting which is input by the input reception device 3.

Figure 17:
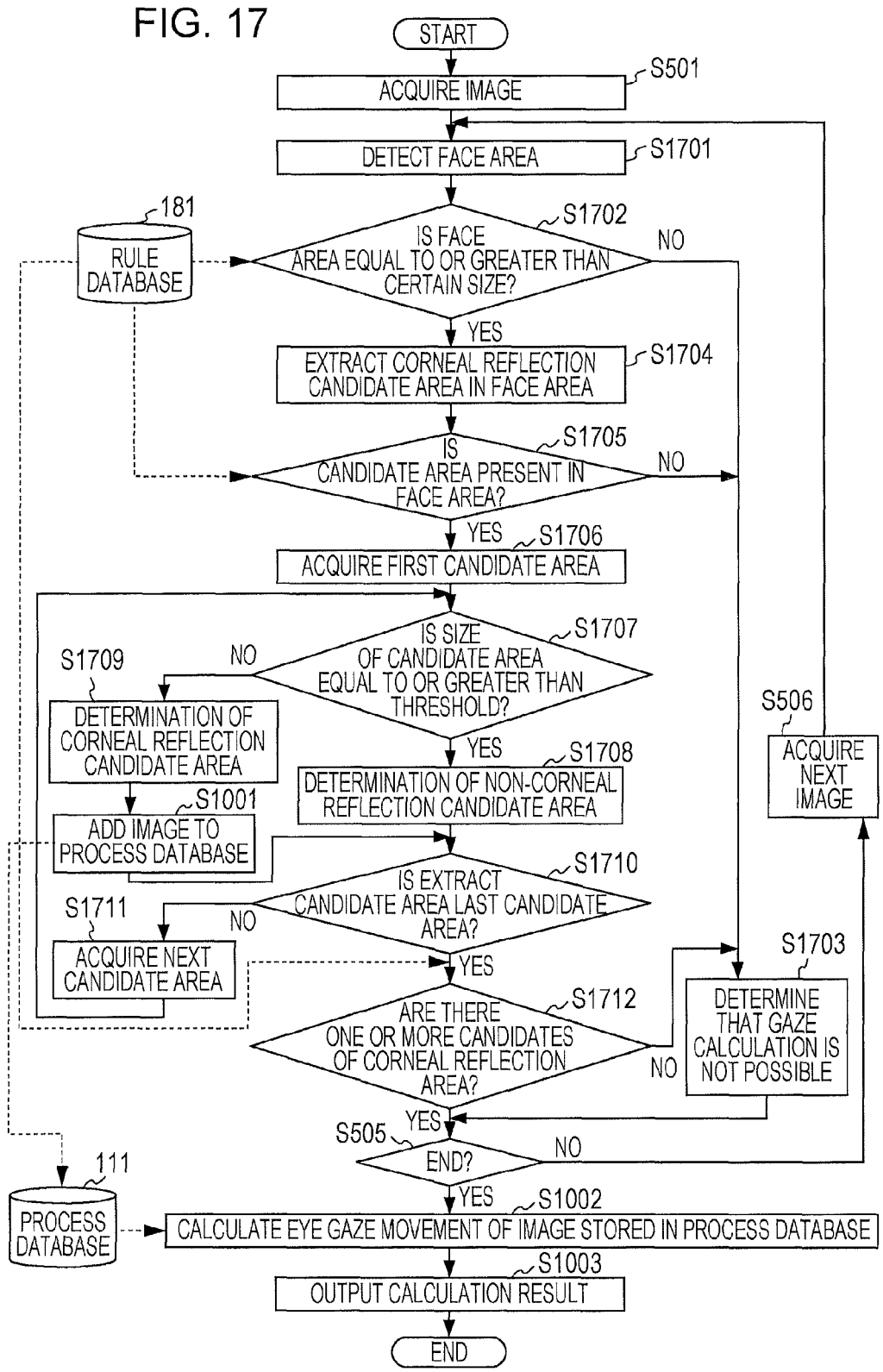
FIG. 17 is a flowchart illustrating a flow of the eye gaze detection process by batch processing performed by the computer of the eye gaze detection apparatus according to the fourth embodiment.

FIG. 17 is a flowchart illustrating a flow of the eye gaze detection process by batch processing performed by the computer of the eye gaze detection apparatus according to the fourth embodiment. FIG. 18 is a diagram illustrating an example of the rule database (part 3).

In the fourth embodiment, a situation in which it is not possible to perform the eye gaze calculation process is assumed depending on a method of the eye gaze detection and usage conditions. Examples includes a case where a user's face is captured small, a case where the candidate of the corneal reflection area is generated in an area other than a face such as metal, or a case where the corneal reflection area is invisible due to the reflection of glasses. In this case, it is not possible to accurately perform the eye gaze calculation process.

First, in step S501 of FIG. 17, the image acquisition unit 11 acquires the image of user's face which is captured by the imaging apparatus 2 from the imaging apparatus 2 via the transmission path. In step S1701, the image acquisition unit 11 performs detection in the face area from the acquired face image.

In step S1702, the eye gaze calculation determination unit 14 refers to a rule database 181 as illustrated in FIG. 18. Then, the eye gaze calculation determination unit 14 determines whether or not the size in the face area detected in step S1701 is equal to or greater than a predetermined size. This is because that when the size in the face area is too small, it is not possible to perform the area of the eye is reduced and thus appropriate eye gaze detection. Meanwhile, the determination in step S1701 includes the determination from the size of the area of an eye in addition to the determination from the area of the entire face. In addition, even though the area of the eye is large, for example, a case where the user is looking aside or a case where the user is looking upside or downside, the corneal reflection area is not present in the image in some cases. The eye gaze calculation determination unit 14 may perform the same process as that when determining that the size in the face area is smaller than a predetermined size in a case where it is determined that the user is looking aside or the user is looking upside or downside based on the positional relationship between parts of the face such as eyes, a nose, and a mouth. Alternatively, the eye gaze calculation determination unit 14 may perform the same process as that when determining that the size in the face area is smaller than a predetermined size in a case where the shape of an eye area in the face area approximates to the shape of the eye area in the case where the user is looking aside or the user is looking upside or downside beyond a predetermined threshold by referring to the information, which is stored in the database (not shown), of the shape of the eye in the case where the user is looking aside or the user is looking upside or downside.

When the shape of the eye is smaller than a certain size (step S1702: No), in step S1703, since the size in the face area is too small, the eye gaze calculation determination unit 14 determines that it is not possible to perform the eye gaze calculation process, and then the process proceeds to step S505. In addition, when the size of the face area is equal to or smaller than a predetermined size, specifically, the size of an eye image in the face area is equal to or smaller than the size which is defined that it is not possible to detect the eye gaze like the case where the user is looking aside or the user is looking upside or downside, it is determined that it is not possible to perform the eye gaze calculation process, and then the process proceeds to step S505. On the other hand, when the shape of the eye is equal to or greater than a certain size (step S1702: Yes), in step S1704, the feature quantity extraction unit 12 extracts the candidate of the corneal reflection area as the feature quantity of the face image acquired by the image acquisition unit 11 in step S1701.

Next, in step S1705, the eye gaze calculation determination unit 14 refers to the rule database 181 as illustrated in FIG. 18. Then, the eye gaze calculation determination unit 14 determines whether or not the candidate of the corneal reflection area is extracted as the feature quantity in the face area. This is because that in a case where the extracted feature quantity is extracted from an area other than the face area and the feature quantity is not extracted in the face area, the extracted feature quantity is not the corneal reflection area.

When the candidate of the corneal reflection area is not extracted (step S1705: No), in step S1703, since the extracted feature quantity is extracted in the area other than the face area and the feature quantity is not extracted in the face area, the eye gaze calculation determination unit 14 determines that it is not possible to perform the eye gaze calculation process, and then the process proceeds to step S505.

On the other hand, when it is determined that the candidate of the corneal reflection area is extracted in step S1705 (step S1705: Yes), since the process of the candidate of the corneal reflection area is performed in order, the first candidate of the corneal reflection area is acquired in step S1706.

In step S1707, the eye gaze calculation determination unit 14 determines that the size of feature quantity in the face area which is extracted by the feature quantity extraction unit 12 is greater than a predetermined value. When the size of feature quantity in the face area is greater than a predetermined value (step S1707: Yes), it is determined that the candidate of the corneal reflection area is not the corneal reflection area (a non-corneal reflection area) in step S1708. That is, it is determined that the candidate of the corneal reflection area is obtained by the reflection of the glasses or the like.

On the other hand, when the size of feature quantity in the face area is not greater than a predetermined value in step S1707 (step S1707: No), it is determined that the candidate of the corneal reflection area is the corneal reflection area in step S1709. Then, the face image is stored in the processing database 111 in step S1001.

In step S1710, it is determined whether or not the next candidate of the corneal reflection area is the last candidate of the corneal reflection area which is extracted in step S1704. When it is not the last candidate (step S1710: No), the next candidate of the corneal reflection area is acquired in step S1711, and the processes after step S1707 are repeated.

On the other hand, when it is the last candidate (step S1710: Yes), it is determined whether or not one or more of candidates of the corneal reflection area are stored in the processing database 111 in step S1712.

When one or more of candidates of the corneal reflection area are stored in the processing database 111 (step S1712: Yes), the process proceeds to step S505. On the other hand, when the candidate of the corneal reflection area is not stored at all (step S1712: No), in step S1703, since the feature quantity is not extracted in the face area, the eye gaze calculation determination unit 14 determines that it is not possible to perform the eye gaze calculation process, and then the process proceeds to step S505.

Then, it is determined whether or not to end the current eye gaze detection process in step S505. When the process does not end (step S505: No), the next face image is acquired in step S506 and the processes after step S1901 are repeated.

On the other hand, when it is determined to end the present eye gaze detection process in step S505 (step S505: Yes), in step S1002, the eye gaze calculation unit 15 performs the eye gaze calculation process based on the feature quantity of the face image stored in the processing database 111 in step S1001.

Then, in step S1003, the result output unit 16 outputs the result of the eye gaze detection process which is performed in step S1002.

Meanwhile, in the fourth embodiment, the face area and the candidate of the corneal reflection area are used for description; however, a technology for more accurately extracting an input face image of a user by using a two-dimensional template may be used (for example, refer to Japanese Laid-open Patent Publication No. 2001-22933). In addition, it is possible to use a technology for detecting a reflection illumination part of the glasses from a captured image of a user wearing glasses (for example, refer to Japanese Laid-open Patent Publication No. 2001-167284).

Figure 19:
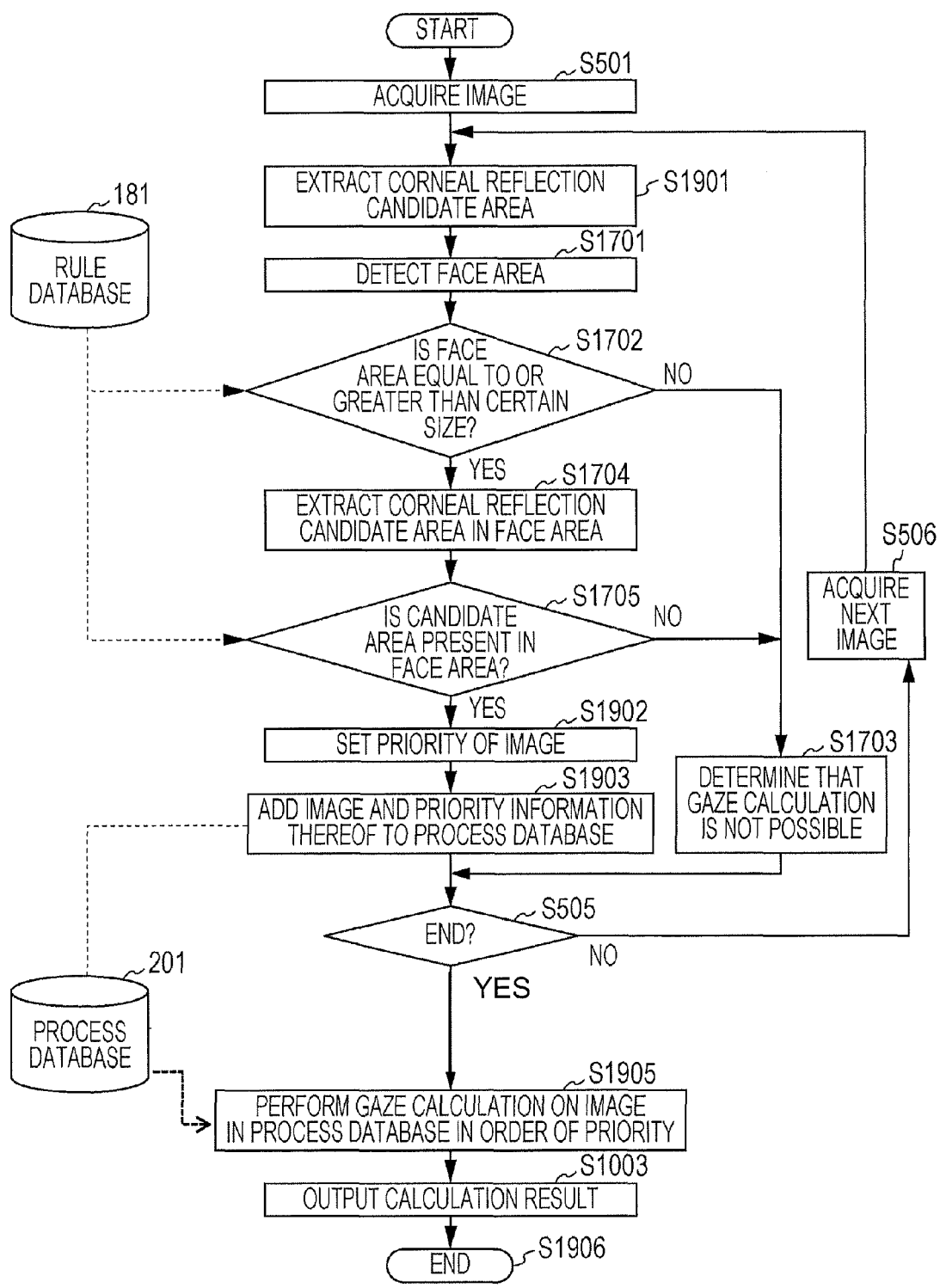
FIG. 19 is a flowchart illustrating a flow of the eye gaze detection process by batch processing performed by the computer of the eye gaze detection apparatus according to the fifth embodiment.

FIG. 19 is a flowchart illustrating a flow of the eye gaze detection process by batch processing performed by the computer of the eye gaze detection apparatus according to the fifth embodiment. FIG. 20 is a diagram illustrating an example of the processing database (part 2).

In fifth embodiment, whether or not the eye gaze calculation process is performed is determined and it is also assumed a case where the eye gaze calculation process is desired to be performed in an order other than in a time-series order. In such a case, the eye gaze calculation process is performed only when desired, and the eye gaze calculation process may be performed in a desired order. In addition, whether or not the eye gaze calculation process is desired is determined by using the information on the face area and the candidate of the corneal reflection area.

First, in step S501 of FIG. 19, the image acquisition unit 11 acquires the image of user's face captured by the imaging apparatus 2 from the imaging apparatus 2 via the transmission path. Next, in step S1901, the feature quantity extraction unit 12 extracts the candidate of the corneal reflection area as the feature quantity of the face image acquired by the image acquisition unit 11 in step S501. Then, in step S1701, the image acquisition unit 11 performs detection in the face area from the acquired face image.

In step S1702, the eye gaze calculation determination unit 14 refers to the rule database 181 as illustrated in FIG. 18. Then, the eye gaze calculation determination unit 14 determines whether or not the size in the face area which is detected in step S1701 is equal to or greater than a predetermined size.

When the size in the face area is smaller than a certain size (step S1702: No), in step S1703, since the size in the face area is too small, the eye gaze calculation determination unit 14 determines that it is not possible to perform the eye gaze calculation process, and then the process proceeds to step S505. On the other hand, when the size in the face area is equal to or greater than a certain size (step S1702: Yes), in step S1704, the feature quantity extraction unit 12 detects the candidate of the corneal reflection area as the feature quantity in the face area which is detected by the image acquisition unit 11 in step S1701.

Next, in step S1705, the eye gaze calculation determination unit 14 refers to the rule database 181 as illustrated in FIG. 18. Then, the eye gaze calculation determination unit 14 determines whether or not the candidate of the corneal reflection area is extracted as the feature quantity in the face area.

When the candidate of the corneal reflection area is not possible to be detected (step S1705: No), in step S1703, since the extracted feature quantity is extracted in the area other than the face area and the feature quantity is not extracted in the face area, the eye gaze calculation determination unit 14 determines it is not possible to perform the eye gaze calculation process, and then the process proceeds to step S505.

On the other hand, when it is determined that the candidate of the corneal reflection area is extracted in step S1705 (step S1705: Yes), in step S1902, the user input receiving unit 1603 receives the processing priority setting which is input by the input reception device 3. For example, in consideration of calculation accuracy of the eye gaze calculation process, the face image having a large number of candidates of the corneal reflection area is set to have higher processing priority than the face image having a small number of candidates of the corneal reflection area. In addition, when the plurality of face images are detected from the acquired same face image, in consideration of calculation accuracy of the eye gaze calculation process, the large sized face area is set to have the high priority. Accordingly, it is possible to perform the eye gaze detection process for a person who is close to the eye gaze detection apparatus.

Then, in step S1903, the processing priority setting unit 1602 associates the feature quantity in the face area extracted in step S1704 with the priority of performing the eye gaze calculation process, and then stores the set priority in a processing database 201 as illustrated in FIG. 20.

Then, it is determined whether or not to end the current eye gaze detection process in step S505. When the process does not end (step S505: No), the next face image is acquired in step S506 and the processes after step S1901 are repeated.

On the other hand, when it is determined to end the present eye gaze detection process in step S505 (step S505: Yes), in step S1905, the eye gaze calculation unit 15 performs the eye gaze calculation process based on the feature quantity of the face image stored in the processing database 201 in order of the priority in step S1903.

Then, in step S1003, the result output unit 16 outputs the result of the eye gaze detection process which is performed in step S1905.

Figure 21A:
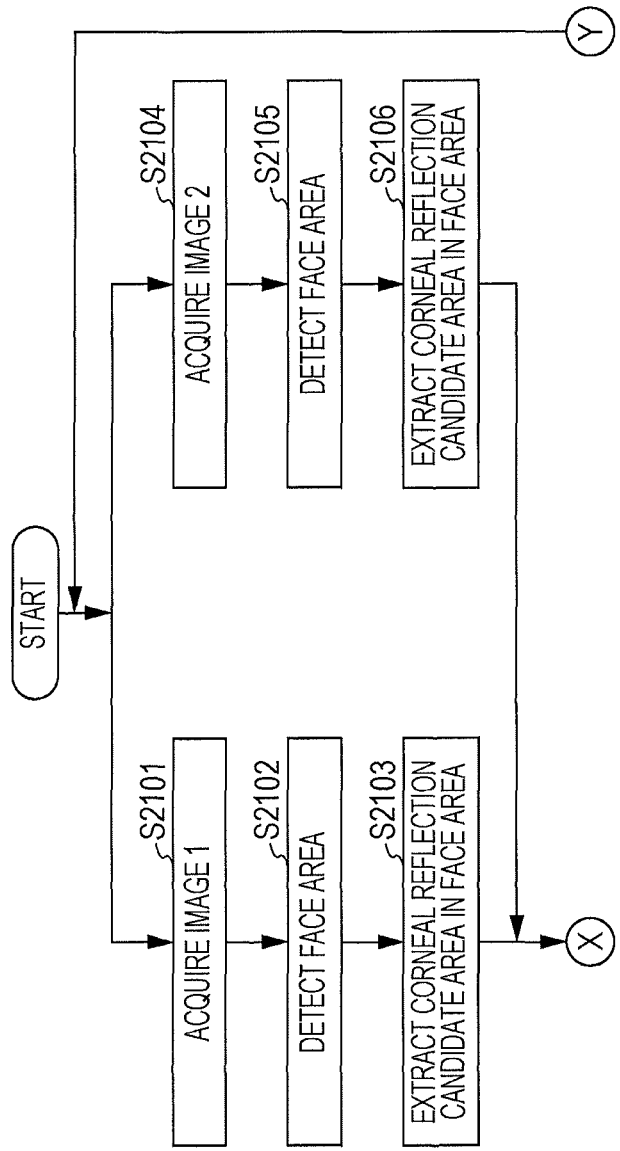

FIGS. 21A and 21B are flowcharts illustrating an eye gaze detection process by serial processing performed by a computer of an eye gaze detection apparatus according to a sixth embodiment. FIG. 22 is a diagram illustrating an example of an overlapping database. FIG. 23 is a diagram illustrating an example of the rule database (part 4). FIGS. 24A and 24B are diagrams illustrating an example of an overlapped image.

In the sixth to eighth embodiments which will be described later, the imaging apparatus 2 is configured to include a plurality of cameras. In this case, spaces which are captured by each of the imaging apparatuses 2 are overlapped with each other. In regard to a user in the overlapped space, the same eye gaze information is output from each of the plurality of imaging apparatuses 2. For this reason, it is possible to reduce a load of calculation process when performing the eye gaze calculation process by avoiding repeatedly calculating the same eye gaze information.

The overlapped area is stored in an overlapping database 221 in advance. For example, an area specified at diagonal coordinates (440,0) and (640,480) of a first face image captured by a "camera 1" which is a first imaging apparatus 2 is stored in the overlapping database 221 as the overlapped area. In addition, an area specified at diagonal coordinates (0,0) and (200,480) of a second face image captured by a "camera 2" which is a second imaging apparatus 2 is stored in the overlapping database 221 as the overlapped area.

First, in step S2101 of FIG. 21, the image acquisition unit 11 acquires a user's first face image captured by a first imaging apparatus 2 from the first imaging apparatus 2 via transmission path. In step S2102, the image acquisition unit 11 performs detection in the first face area from the acquired first face image. In step S2103, the feature quantity extraction unit 12 extracts the candidate of a first corneal reflection area as the feature quantity in the first face area detected by the image acquisition unit 11 in step S2102 and then stores the extracted candidate in an overlapping database 221 as illustrated in FIG. 22.

In addition, in step S2104, the image acquisition unit 11 acquires a user's second face image captured by a second imaging apparatus 2 from the second imaging apparatus 2 via transmission path. In step S2105, the image acquisition unit 11 performs detection of the second face area from the acquired second face image. In step S2106, the feature quantity extraction unit 12 extracts the candidate of a second corneal reflection area as the feature quantity of the second face area detected by the image acquisition unit 11 in step S2105 and then stores the extracted candidate in an overlapping database 221 as illustrated in FIG. 22.

Steps S2101 to S2103 are performed in parallel with steps S2104 to S2106.

In step S2107, the eye gaze calculation determination unit 14 refers to the overlapping database 221. Then, the eye gaze calculation determination unit 14 determines whether or not the feature quantities of the first and second face images which are extracted by the feature quantity extraction unit 12 are within the overlapped area of the first and second face images acquired by the image acquisition unit 11.

When the feature quantities of the first and second face images are not within the overlapped area in the first and second face images (step S2107: No), in step S2108, the eye gaze calculation unit 15 performs the user's eye gaze calculation process based on each of the feature quantities of the first and second face images. Then, in step S2109, the result output unit 16 outputs the result of the performed eye gaze calculation process, and then the process proceeds to step S505.

On the other hand, when it is determined that the feature quantities of the first and second face images are within the overlapped area of the first and second face images in step S2107 (step S2107: Yes), in step S2110, the eye gaze calculation determination unit 14 refers to a rule database 231 as illustrated in FIG. 23. The rule database 231 includes the rule set in which in a case where the feature quantities of the two face images are within an overlapped area of the two face images, the eye gaze calculation process is performed based on the feature quantity of any one of the face images. This rule set represents that there is a high possibility of obtaining the same result of the eye gaze calculation based on the feature quantities of both of the face images, and thus the eye gaze detection of one side may be sufficient. For example, a case where the feature quantities of the two face images are within the overlapped area of the two face images is a case where the feature quantities of the two face images are within the overlapped areas 2401 and 2402 as illustrated in FIGS. 24A and 24B. Then, when the candidates of the corneal reflection areas of the first and second face areas are not extracted in steps S2103 and S2106 (step S2110: Yes), the process proceeds to step S2116.

When the candidates of the corneal reflection areas of the first and second face areas are extracted in steps S2103 and S2106 (step S2110: No), in step S2111, it is determined whether or not an average likelihood of the candidate of the corneal reflection area in the first face area is higher than the average likelihood of the candidate of the corneal reflection area of the second face area.

When it is determined that the average likelihood of the candidate of the corneal reflection area in the first face area is high (step S2111: Yes), in step S2112, the eye gaze calculation unit 15 performs the user's eye gaze calculation process based on the feature quantity of the first face image. Then, in step S2113, the result output unit 16 outputs the result of the performed eye gaze calculation process, and then the process proceeds to step S505.

On the other hand, when it is determined that the average likelihood of the candidate of the corneal reflection area in the first face area is not high, that is, the average likelihood of the candidate of the corneal reflection area of the second face area is high (step S2111: No), in step S2114, the eye gaze calculation unit 15 performs the user's eye gaze calculation process based on the second feature quantity of the face image. Here, the average likelihood of the candidate of the corneal reflection area is a criterion which is in consideration of the calculation accuracy of the eye gaze calculation process, and is set in advance.

Then, in step S2115, the result output unit 16 outputs the result of the performed eye gaze calculation process, and the process proceeds to step S505.

In addition, in step S2110, when the candidates of the corneal reflection areas in the first and second face areas are not extracted at all in steps S2103 and S2106 (step S2110: Yes), in step S2116, since the feature quantity is not extracted, the eye gaze calculation determination unit 14 determines that it is not possible to perform the eye gaze calculation process, and then the process proceeds to step S505.

Then, it is determined whether or not to end the current eye gaze detection process in step S505. When the process does not end (step S505: No), the process returns to step S2101 and S2104.

By performing the eye gaze detection process as described above, when there are the same candidates of the corneal reflection area in the plurality of face images, it is possible to perform the eye gaze calculation process on any one of the face images. In addition, when there are the face image on which the eye gaze calculation process is easily performed and the face image on which the eye gaze calculation process is not easily performed, which are for example, two face images in the face images in which the reflection by the glasses is generated, it is possible to select the face image on which the eye gaze calculation process is easily performed. Further, it is possible to select the face image having the higher calculation accuracy of the eye gaze calculation process by setting the criterion in consideration of the calculation accuracy of the eye gaze calculation process. Therefore, it is possible to reduce a processing load and a deterioration of the calculation accuracy when performing the eye gaze calculation process.

In addition, in the above description, while examples in which either one of face images is determined to be subjected to the process are described, in a case where the half face is captured on each image, it is possible to perform the process by combining the two face images with each other. Further, the overlapped area may be set in accordance with the distance from the imaging apparatus 2 and may be set in consideration of the positional relationship between the two imaging apparatuses 2 and installation conditions thereof, for example, an installation angle.

Figure 25:
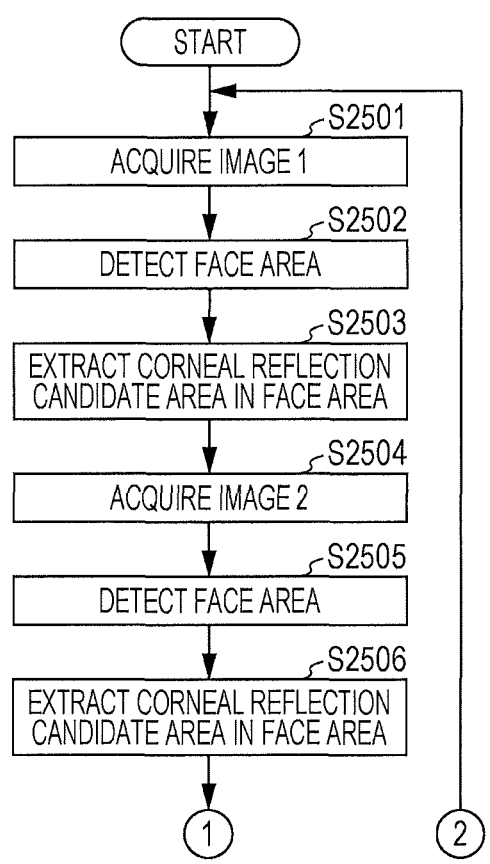
FIG. 25 is a flowchart (part 1) illustrating a flow of an eye gaze detection process by serial processing performed by a computer of an eye gaze detection apparatus according to the seventh embodiment.
Figure 26:
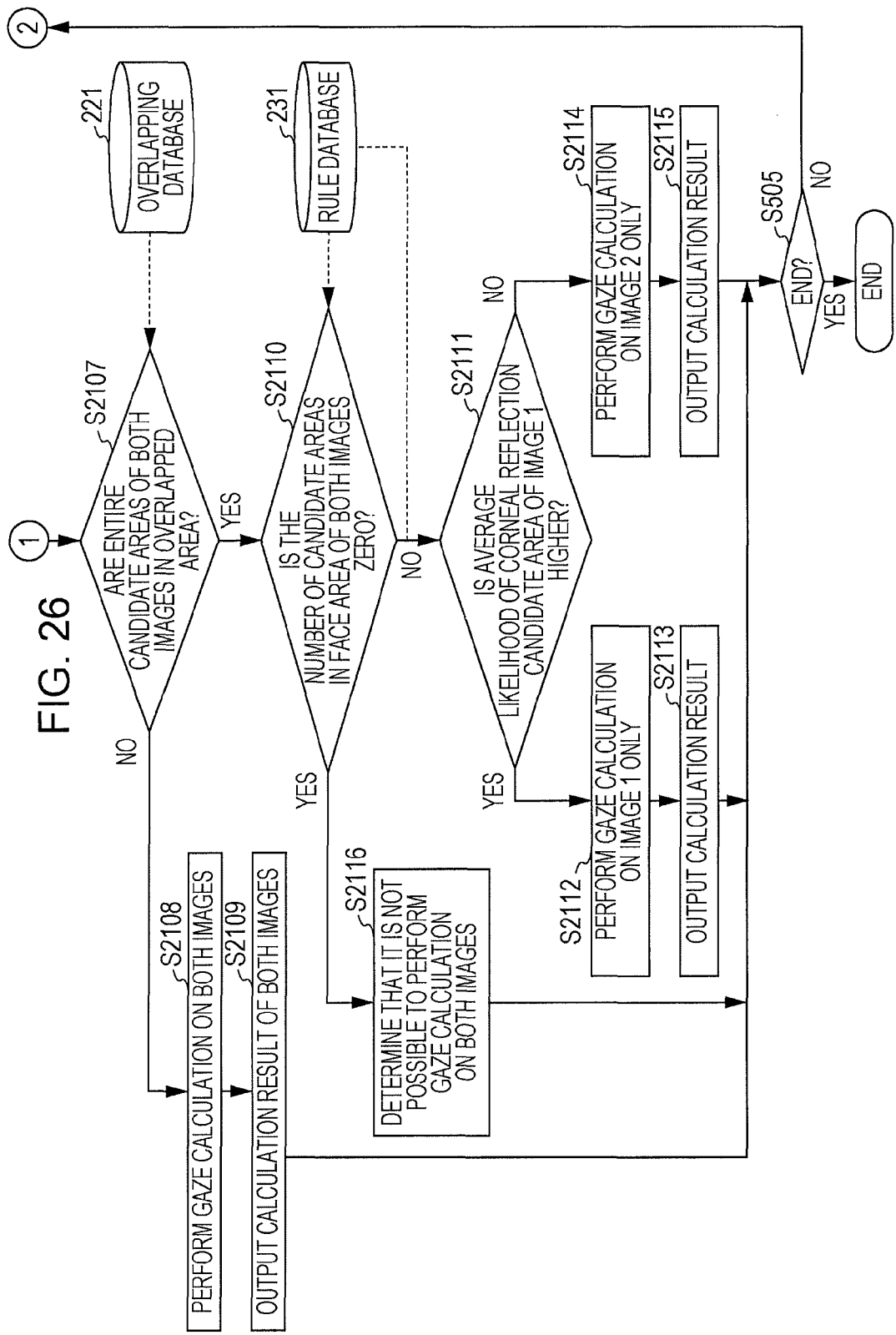
FIG. 26 is a flowchart (part 2) illustrating the flow of the eye gaze detection process by the serial processing performed by the computer of an eye gaze detection apparatus according to the seventh embodiment.

FIGS. 25 and 26 are flowcharts illustrating an eye gaze detection process by serial processing performed by a computer of an eye gaze detection apparatus according to a seventh embodiment.

In the described sixth embodiment, steps S2101 to S2103 are performed in parallel with steps S2104 to S2106.

In the seventh embodiment, steps S2104 to S2106 are performed after performing steps S2101 to S2103. That is, it is possible to perform the eye gaze detection process even when the two face images are not captured at the same time but captured within a certain time range.

Figure 27:
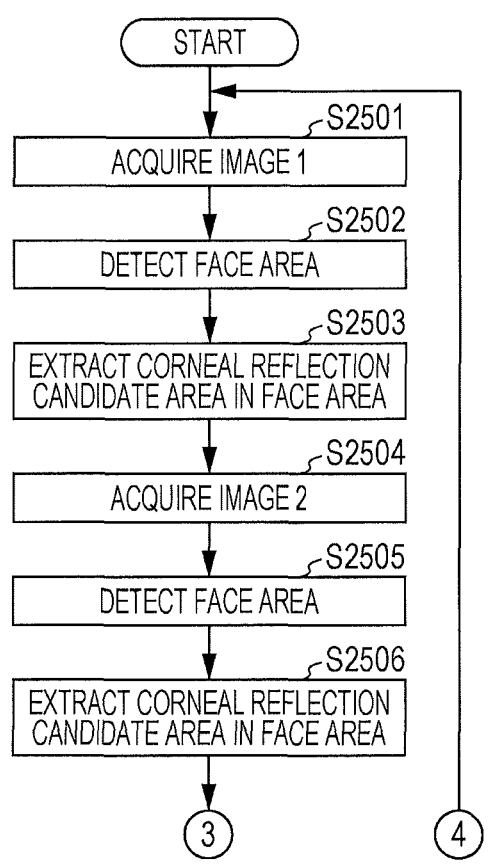
FIG. 27 is a flowchart (part 1) illustrating a flow of an eye gaze detection process by batch processing performed by a computer of an eye gaze detection apparatus according to the eighth embodiment.
Figure 28:
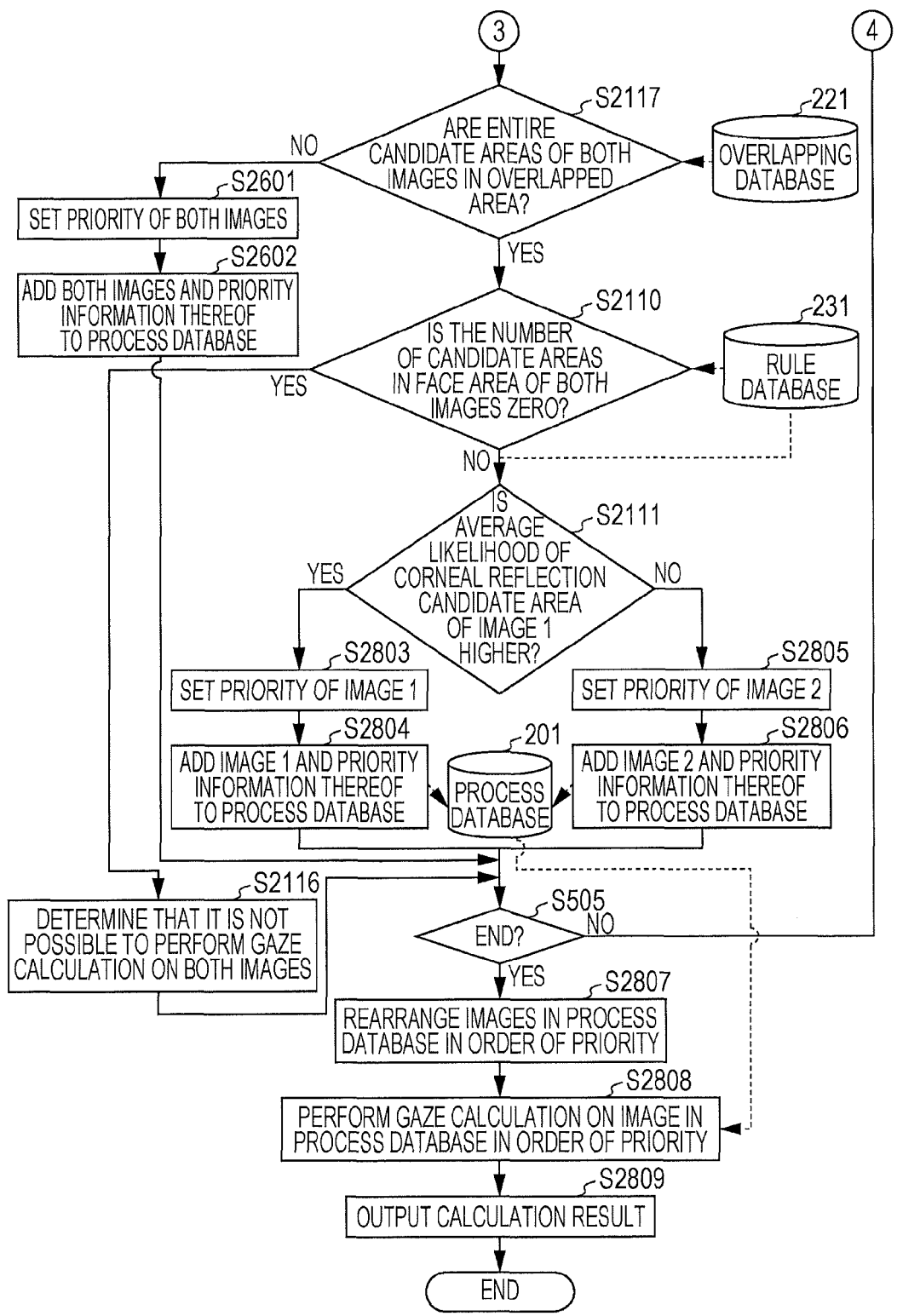
FIG. 28 is a flowchart (part 2) illustrating the flow of the eye gaze detection process by the batch processing performed by the computer of the eye gaze detection apparatus according to the eighth embodiment.

FIGS. 27 and 28 are flowcharts illustrating a flow of an eye gaze detection process by batch processing performed by a computer of an eye gaze detection apparatus according to the eighth embodiment.

In the eighth embodiment, the determination result obtained in step S2111 of the seventh embodiment is set as a priority.

That is, in step S2111, when it is determined that the average likelihood of the candidate of the corneal reflection area in the first face area is higher than that in the second face area (step S2111: Yes), the first face image is set to have a higher priority in step S2803. It is preferable that the priority is set based on characteristics such as likelihood or detection accuracy of the candidate of the corneal reflection area. Then, in step S2804, the first face image is associated with a priority and the set priority is stored in the processing database 201, and then the process proceeds to step S505.

In addition, in step S2111, when it is determined that the average likelihood of the candidate of the corneal reflection area in the first face area is not higher than that in the second face area (step S2111: No), the second face image is set to have a higher priority in step S2805. Then, in step S2806, the second face image is associated with the priority and the set priority is stored in the processing database 201, and then the process proceeds to step S505.

Thereafter, when it is determined that the process ends in step S505 (step S505: Yes), in step S2807, the face images in the processing database 201 are rearranged in a priority order (sorting).

In step S2808, the eye gaze calculation unit 15 performs the eye gaze calculation process based on the feature quantity of the face image in the sorted priority order.

Then, in step S2809, the result output unit 16 outputs the result of the performed eye gaze calculation process.

It is possible to control the load of calculation process by performing the eye gaze calculation process based on the priority described above, for example, by performing the eye gaze calculation process on both eyes after simply performing the eye gaze calculation process on one side of eyes.

Figure 29:
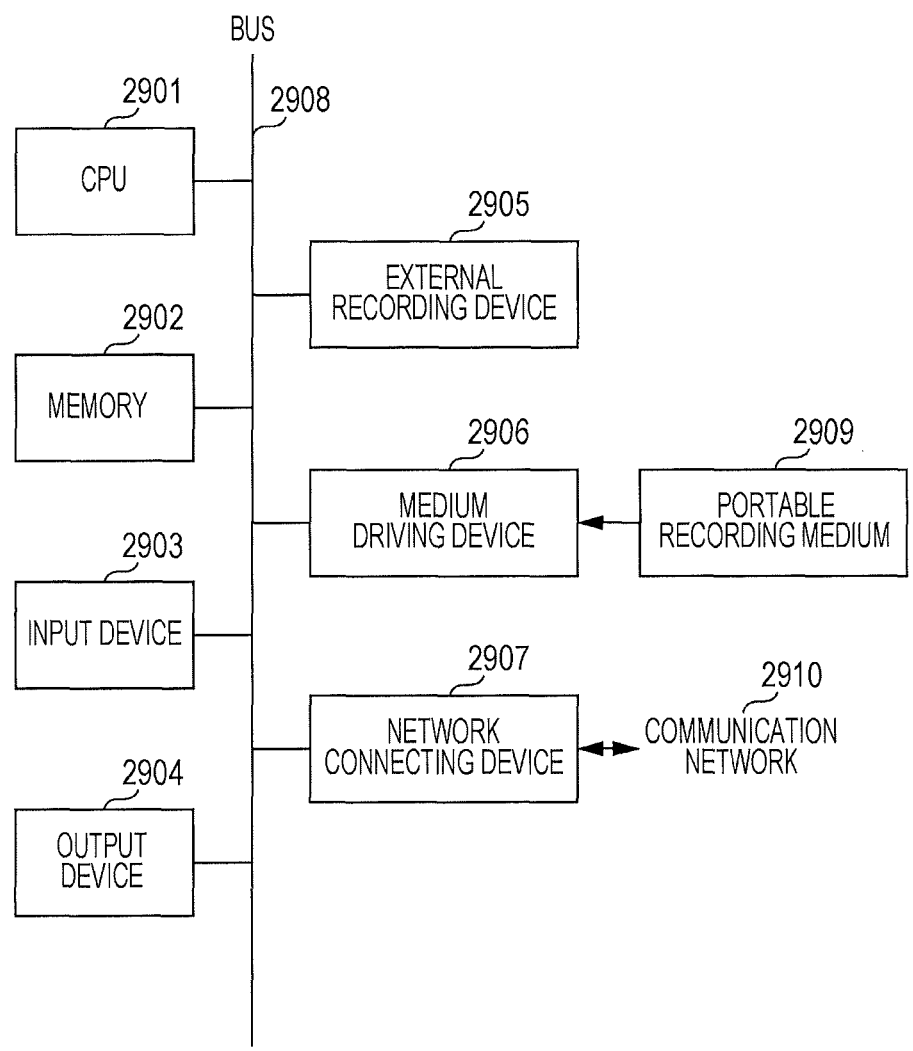
FIG. 29 is a configuration example of an information processing apparatus.

FIG. 29 is a configuration example of the information processing apparatus.

The eye gaze detection apparatuses 1A, 1B, and 1C in FIG. 1 may be realized by using, for example, the information processing apparatus (the computer) in FIG. 29. The information processing apparatus illustrated in FIG. 29 includes a central processing unit (CPU) 2901, a memory 2902, an input device 2903, an output device 2904, an external recording device 2905, a medium driving device 2906, and a network connecting device 2907. These are connected to each other via a bus 2908.

The memory 2902 is a semiconductor memory, for example, a read only memory (ROM), a random access memory (RAM), and a flash memory, and stores a program and data which are used in the eye gaze detection process which is performed by the eye gaze detection apparatuses 1A, 1B, and 1C. For example, the CPU 2901 performed the above described eye gaze detection process by performing the program by using the memory 2902.

The input device 2903 may be a keyboard, a pointing device, or the like and is used for an input of instruction or information from an operator. The output device 2904 may be a display device, a printer, a speaker, or the like and is used to pose queries to the operator or output a processing result.

The external recording device 2905 may be a magnetic disk device, a magneto-optical disk device, a tape device, or the like. This external recording device 2905 includes a hard disk drive. The information processing apparatus stores a program and data in the external recording device 2905 in advance and the stored program and data may be used by being loaded into the memory 2902.

A medium driving device 2906 drives a portable recording medium 2909 and accesses to the record contents. The portable recording medium 2909 may be a memory device, a flexible disk, an optical disk, a magneto-optical disk, or the like. The portable recording medium 2909 includes a compact disk read only memory (CD-ROM), a digital versatile disk (DVD), a universal serial bus (USB), a memory, or the like. The operator stores a program and data in the portable recording medium 2909 and the stored program and data may be used by being loaded into the memory 2902.

In this way, a computer readable recording medium which stores the program and data which are used for the eye gaze detection process includes a physical (non-temporary) recording medium such as the memory 2902, the external recording device 2905, and the portable recording medium 2909.

The network connecting device 2907 is connected to the communication network 2910, and is a communication interface for performing data conversion in accordance with communication. The information processing apparatus receives the program and data from the external device via the network connecting device 2907, and the received program and data may be used by being loaded into the memory 2902.

While embodiments of the disclosure and advantages thereof are described in detail, those skilled in the art will perform various modifications, additions, and omissions without departing from the scope of the technology which is clearly described in the claims.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. An eye gaze detection apparatus comprising:
   at least one processor; and
   at least one memory which store a plurality of instructions, which when executed by the at least one processor, cause the at least one processor to execute:
      acquiring a face image of a user from an imaging apparatus, the face image being captured by the imaging apparatus;
      extracting a feature quantity of the acquired face image;
      determining whether or not an eye gaze calculation process for the user is to be performed by referring to a rule database, based on the extracted feature quantity, the rule database storing a rule set associating a condition including the feature quantity of the face image with information indicating whether or not the eye gaze calculation process is performed; and
      performing the eye gaze calculation process for the user, based on the feature quantity of the face image acquired by the image acquisition unit, when it is determined that the eye gaze calculation process is to be performed.

2. The eye gaze detection apparatus according to claim 1, wherein the at least one processor further executes:
   outputting a result of the eye gaze calculation process.

3. The eye gaze detection apparatus according to claim 2, wherein the at least one processor further executes:
   comparing the feature quantity of the face image in a current frame with the feature quantity of the face image in a previous frame,
   wherein the rule database includes a rule set in which the eye gaze calculation process is not performed in a case where the feature quantity of the face image in the current frame coincides with the feature quantity of the face image in the previous frame at a predetermined ratio or higher,
   wherein the determining determines that the eye gaze calculation process is not performed, based on a comparison result, when the feature quantity of the face image in the current frame coincides with the feature quantity of the face image in the previous frame at the predetermined ratio or higher, and
   wherein the outputting outputs the result of the eye gaze calculation process which is performed based on the feature quantity of the face image in the previous frame.

4. The eye gaze detection apparatus according to claim 1, wherein the at least one processor further executes:
   comparing the feature quantity of the face image in a current frame with the feature quantity of the face image in a previous frame
   wherein the rule database includes a rule set in which the eye gaze calculation process is not performed when the number of the feature quantities of the face image in the current frame is changed equal to or more than a predetermined number in comparison with the number of the feature quantities of the face image in the previous frame and a changed quantity, in a predetermined direction, of the feature quantity which changes between in the current frame and in the previous frame is within a predetermined value, and
   wherein the determining determines that the eye gaze calculation process is not performed, based on a comparison result, when the number of the feature quantities of the face image in the current frame is changed equal to or more than the predetermined number in comparison with the number of the feature quantities of the face image in the previous frame and the changed quantity, in the predetermined direction, of the feature quantity which changes between in the current frame and in the previous frame is within the predetermined value.

5. The eye gaze detection apparatus according to claim 1, wherein the acquiring specifies a right eye peripheral area and a left eye peripheral area in a predetermined range from the acquired face image,
wherein the rule database includes a rule set in which the eye gaze calculation process is not performed when pixels on both sides of feature quantities in the right eye peripheral area and the left eye peripheral area are less than a predetermined number of white pixels, and
wherein the determining determines that the eye gaze calculation process is not performed when the pixels on the both sides of the feature quantities in the specified right eye peripheral area and the left eye peripheral area are less than the predetermined number of white pixels.

6. The eye gaze detection apparatus according to claim 1, wherein the at least one processor further executes:
detecting a face area from the acquired face image,
wherein the rule database includes a rule set in which the eye gaze calculation process is not performed when a size in the face area is smaller than a predetermined value, and
wherein the determining determines that the eye gaze calculation process is not performed when the size in the face area is smaller than the predetermined value.

7. The eye gaze detection apparatus according to claim 1, wherein the at least one processor further executes:
detecting a face area from the acquired face image,
wherein the extracting extracts the feature quantity in the face area,
wherein the rule database includes a rule set in which the eye gaze calculation process is not performed when the feature quantity is not extracted in the face area, and
wherein the determining determines that the eye gaze calculation process is not performed when the feature quantity is not extracted in the face area.

8. The eye gaze detection apparatus according to claim 1, wherein the at least one processor further executes:
detecting a face area from the acquired face image,
wherein the extracting extracts the feature quantity in the face area,
wherein the rule database includes a rule set in which the eye gaze calculation process is not performed when the feature quantity in the face area is out of a predetermined area, and
wherein the determining determines that the eye gaze calculation process is not performed when the feature quantity in the face area is out of the predetermined area.

9. The eye gaze detection apparatus according to claim 1, wherein the at least one processor further executes:
setting a priority by associating the extracted feature quantity with a priority of performing the eye gaze calculation process,
wherein the determining determines that the eye gaze calculation process is performed in accordance with the priority for the feature quantity.

10. The eye gaze detection apparatus according to claim 1,
wherein the acquiring acquires a first face image captured by a first imaging apparatus and a second face image captured by a second imaging apparatus,
wherein the extracting the feature quantities of the first and second face images,
wherein the rule database includes a rule set in which the eye gaze calculation process is performed based on the feature quantity of any one of the face images when the feature quantities of the two face images are within an overlapped area of the two face images, and
wherein the determining determines that the eye gaze calculation process is performed based on the feature quantity of the first face image and/or the feature quantity of the second face image in the case where the extracted feature quantities of the first and second face images are in the overlapped area of the first and second face images.

11. A non-transitory computer-readable recording medium storing a program for causing a computer in an eye gaze detection apparatus to execute an eye gaze detection process comprising:
acquiring a face image of a user from an imaging apparatus, the face image being captured by the imaging apparatus;
extracting a feature quantity of the acquired face image;
determining whether or not an eye gaze calculation process for the user is to be performed by referring to a rule database, based on the extracted feature quantity, the rule database storing a rule set associating a condition including the feature quantity of the face image with information indicating whether or not the eye gaze calculation process is performed; and
performing the eye gaze calculation process for the user, based on the feature quantity of the acquired face image, when it is determined the eye gaze calculation process is to be performed.

12. An eye gaze detection method executed by a computer in an eye gaze detection apparatus, comprising:
acquiring a face image of a user from an imaging apparatus, the face image being captured by the imaging apparatus;
extracting a feature quantity of the acquired face image;
determining whether or not an eye gaze calculation process for the user is to be performed by referring to a rule database, based on the extracted feature quantity, the rule database storing a rule set associating a condition including the feature quantity of the face image with information indicating whether or not the eye gaze calculation process is performed; and
performing the eye gaze calculation process for the user, based on the feature quantity of the acquired face image, when it is determined the eye gaze calculation process is to be performed in the determining.

13. The eye gaze detection method according to claim 12, further comprising:
outputting a result of the performed eye gaze calculation process,
comparing the extracted feature quantity of the face image in a current frame with the feature quantity of the face image in a previous frame,
wherein the rule database includes a rule set in which the eye gaze calculation process is not performed when the feature quantity of the face image in the current frame coincides with the feature quantity of the face image in the previous frame at a predetermined ratio or higher is included,
wherein the determining determines that the eye gaze calculation process is not performed when the feature quantity of the face image in the current frame coincides with the feature quantity of the face image in the previous frame at the predetermined ratio or higher based on a result of the comparing, and
wherein in the outputting the result of the eye gaze calculation process which is performed based on the feature quantity of the face image in the previous frame is output in the outputting.

14. The eye gaze detection method according to claim 12, further comprising:
comparing the feature quantity of the face image in a current frame with the feature quantity of the face image in a previous frame,
wherein the rule database includes a rule set in which the eye gaze calculation process is not performed when the number of the feature quantities of the face image in the current frame is changed equal to or more than a predetermined number in comparison with the number of the feature quantities of the face image in the previous frame and a changed quantity, in a predetermined direction, of the feature quantity which changes between in the current frame and in the previous frame is within a predetermined value, and
wherein the determining determines that the eye gaze calculation process is not performed, based on a result of the comparing, when the number of the feature quantities of the face image in the current frame is changed equal to or more than the predetermined number in comparison with the number of the feature quantities of the face image in the previous frame and the changed quantity, in the predetermined direction, of the feature quantity which changes between in the current frame and in the previous frame is within the predetermined value.

15. The eye gaze detection method according to claim 12, wherein in the acquiring of the image, a right eye peripheral area and a left eye peripheral area in a predetermined area from the acquired face image are specified,
wherein in the rule database, a rule set in which the eye gaze calculation process is not performed when pixels on both sides of feature quantities in the right eye peripheral area and the left eye peripheral area are less than a predetermined number of white pixels is included, and
wherein in the determining of eye gaze calculation, it is determined that the eye gaze calculation process is not performed in the case where the pixels on both sides of feature quantities in the right eye peripheral area and the left eye peripheral area, which are specified as above, are less than a predetermined number of white pixels.

16. The eye gaze detection method according to claim 12, further comprising:
detecting the face area from the acquired face image,
wherein in the rule database, a rule set in which the eye gaze calculation process is not performed in a case where the size in the face area is smaller than a predetermined value is included, and
wherein in the determining of the eye gaze calculation, it is determined that the eye gaze calculation process is not performed in the case where the detected size in the face area is smaller than a predetermined value.

17. The eye gaze detection method according to claim 12, further comprising:
detecting a face area from the acquired face image,
wherein in the extracting of the feature quantity, the detected feature quantity in the face area is extracted,
wherein in the rule database, a rule set in which the eye gaze calculation process is not performed in a case where the feature quantity is not extracted in the face area is included, and
wherein in the determining of the eye gaze calculation, it is determined that the eye gaze calculation process is not performed in the case where the feature quantity is not extracted in the face area.

18. The eye gaze detection method according to claim 12, further comprising:
detecting a face area from the acquired face image,
wherein in the extracting of the feature quantity, the detected feature quantity in the face area is extracted,
wherein in the rule database, a rule set in which the eye gaze calculation process is not performed in a case where the feature quantity in the face area is out of a predetermined range is included, and
wherein in the determining of the eye gaze calculation, it is determined that the eye gaze calculation process is not performed in the case where the extracted feature quantity in the face area is out of a predetermined range.

19. The eye gaze detection method according to claim 12, further comprising:
setting a priority by associating the extracted feature quantity with a priority of performing the eye gaze calculation process, and
wherein in the determining of the eye gaze calculation, it is determined that the eye gaze calculation process is performed in accordance with the priority of the extracted feature quantity.

20. The eye gaze detection method according to claim 12, wherein in the acquiring of the image, a face image captured by a first imaging apparatus and a second face image captured by a second imaging apparatus are acquired,
wherein in the extracting of the feature quantity, the feature quantities of the acquired first and second face images are extracted,
wherein in the rule database, a rule set in which the eye gaze calculation process is performed based on the feature quantity of any one of the face images in a case where the feature quantities of the two face images are within an overlapped area of the two face images is included, and
wherein in the determining of the eye gaze calculation, it is determined that the eye gaze calculation process is performed based on the feature quantity of the first face image and/or the feature quantity of the second face image in the case where the feature quantities, which are extracted, of the first and second face images are in the overlapped area of the acquired first and second face images.

* * * * *